(12) United States Patent
Wallace et al.

(10) Patent No.: US 9,918,681 B2
(45) Date of Patent: Mar. 20, 2018

(54) SYSTEM AND METHOD FOR VIRTUALLY TRACKING A SURGICAL TOOL ON A MOVABLE DISPLAY

(75) Inventors: Dan Wallace, Santa Cruz, CA (US); Greg Stahler, San Jose, CA (US); Jaime Waydo, Campbell, CA (US); Aaron Grogan, Scotts Valley, CA (US)

(73) Assignee: Auris Surgical Robotics, Inc., Redwood City, CA (US)

( * ) Notice: Subject to any disclaimer, the term of this patent is extended or adjusted under 35 U.S.C. 154(b) by 250 days.

(21) Appl. No.: 13/618,915

(22) Filed: Sep. 14, 2012

(65) Prior Publication Data

US 2013/0072787 A1    Mar. 21, 2013

Related U.S. Application Data

(60) Provisional application No. 61/535,753, filed on Sep. 16, 2011, provisional application No. 61/585,580, (Continued)

(51) Int. Cl.
*A61B 90/00* (2016.01)
*A61B 6/12* (2006.01)
(Continued)

(52) U.S. Cl.
CPC .............. *A61B 6/12* (2013.01); *A61B 6/4405* (2013.01); *A61B 6/462* (2013.01); *A61B 6/463* (2013.01);
(Continued)

(58) Field of Classification Search
CPC .... A61B 6/40; A61B 6/42; A61B 6/46; A61B 6/461; A61B 6/462; A61B 6/463;
(Continued)

(56) References Cited

U.S. PATENT DOCUMENTS 5,134,390 A    7/1992 Kishimoto et al.
5,526,812 A *  6/1996 Dumoulin ............... G06F 3/013
                                                345/7
(Continued)

OTHER PUBLICATIONS

International search report and written opinion dated Feb. 5, 2013 for PCT/US2012/055634.
(Continued)

*Primary Examiner* — Tse Chen
*Assistant Examiner* — Nate S Sunwoo
(74) *Attorney, Agent, or Firm* — Knobbe Martens Olson & Bear LLP

(57) ABSTRACT

The invention comprises a virtual window system that creates a visual coherency between the image of the patient and his or her anatomy and the patient by aligning the image of the patient anatomy on the display to the patient and presenting the image to the user that feels as if the user is looking directly into the patient through the display. The invention is designed to also display medical devices, such as a minimally invasive tool. The system substantially unifies the coordinate systems of the patient, the medical device, the display, and the physician's hands. The invention creates a visual coherency between the motion of the medical device in the image and the motion of the physician's hands manipulating the device. This invention also creates a visual coherency between the motion of the image in the display and of that display.

27 Claims, 33 Drawing Sheets

Related U.S. Application Data filed on Jan. 11, 2012, provisional application No. 61/615,141, filed on Mar. 23, 2012.

(51) Int. Cl.
| | | |
|---|---|---|
| *A61B 6/00* | (2006.01) | |
| *A61B 34/20* | (2016.01) | |
| *A61B 8/00* | (2006.01) | |
| *A61B 90/50* | (2016.01) | |

(52) U.S. Cl.
CPC .............. *A61B 6/467* (2013.01); *A61B 6/487* (2013.01); *A61B 6/5235* (2013.01); *A61B 6/547* (2013.01); *A61B 34/20* (2016.02); *A61B 90/50* (2016.02); *A61B 8/00* (2013.01); *A61B 2034/2051* (2016.02); *A61B 2090/372* (2016.02); *A61B 2090/504* (2016.02); *A61B 2090/508* (2016.02); *F04C 2270/041* (2013.01)

(58) Field of Classification Search
CPC ......... A61B 6/465; A61B 6/466; A61B 6/467; A61B 6/468; A61B 6/469; A61B 6/485; A61B 6/486; A61B 6/487; A61B 6/488; A61B 6/5288; A61B 6/547; A61B 6/584; A61B 6/587; A61B 6/588; A61B 6/589; A61B 8/0841; A61B 8/085; A61B 8/46; A61B 8/461; A61B 8/462; A61B 8/463; A61B 8/466; A61B 8/467; A61B 8/468; A61B 8/52; A61B 8/5207; A61B 8/5238; A61B 8/5253; A61B 8/5261; A61B 8/5284; A61B 19/20; A61B 19/50; A61B 19/52; A61B 19/5212; A61B 19/5225; A61B 19/5244
USPC ....... 600/415, 420, 424, 425, 426, 429, 431, 600/443
See application file for complete search history.

(56) References Cited

U.S. PATENT DOCUMENTS

| | | | |
|---|---|---|---|
| 5,694,142 A | | 12/1997 | Dumoulin et al. |
| 5,808,665 A | | 9/1998 | Green |
| 5,831,614 A | * | 11/1998 | Tognazzini ............. G06F 3/033 345/156 |
| 6,038,467 A | * | 3/2000 | De Bliek ............... A61B 90/36 600/424 |
| 6,425,865 B1 | | 7/2002 | Salcudean et al. |
| 6,466,198 B1 | * | 10/2002 | Feinstein .............. G06F 1/1626 345/158 |
| 6,690,964 B2 | | 2/2004 | Bieger et al. |
| 7,203,277 B2 | | 4/2007 | Birkenbach et al. |
| 7,774,044 B2 | | 8/2010 | Sauer et al. |
| 7,880,739 B2 | | 2/2011 | Long et al. |
| 2002/0077533 A1 | * | 6/2002 | Bieger et al. ................ 600/300 |
| 2002/0120188 A1 | | 8/2002 | Brock et al. |
| 2004/0047044 A1 | * | 3/2004 | Dalton ................... A61B 6/462 359/630 |
| 2004/0263535 A1 | * | 12/2004 | Birkenbach ............ A61B 6/032 345/629 |
| 2005/0193451 A1 | * | 9/2005 | Quistgaard .......... A61B 5/6843 414/1 |
| 2006/0173290 A1 | | 8/2006 | Lavallee et al. |
| 2008/0183188 A1 | * | 7/2008 | Carls .................... A61B 5/0488 606/130 |
| 2008/0306490 A1 | * | 12/2008 | Lakin .................... A61B 5/064 606/130 |
| 2009/0248036 A1 | * | 10/2009 | Hoffman et al. ............. 606/130 |
| 2009/0322671 A1 | | 12/2009 | Scott et al. |
| 2010/0039506 A1 | * | 2/2010 | Sarvestani ............. A61B 34/20 348/65 |
| 2010/0053151 A1 | | 3/2010 | Marti et al. |
| 2010/0161129 A1 | * | 6/2010 | Costa et al. .................. 700/259 |
| 2010/0295931 A1 | | 11/2010 | Schmidt |
| 2010/0328455 A1 | * | 12/2010 | Nam .................... G06T 7/0042 348/135 |
| 2011/0248987 A1 | | 10/2011 | Mitchell |
| 2014/0357984 A1 | | 12/2014 | Wallace et al. |

OTHER PUBLICATIONS

European search report and written opinion dated Aug. 24, 2015 for EP Application No. 12832283.1.
Nikou, et al. Augmented reality imaging technology for orthopaedic surgery. Operative Techniques in Orthopaedics 10.1 (2000): 82-86.
Office action dated Feb. 17, 2017 for U.S. Appl. No. 14/286,793.
Office action dated Mar. 11, 2015 for U.S. Appl. No. 14/286,793.
Office action dated Aug. 7, 2014 for U.S. Appl. No. 14/286,793.
Office action dated Sep. 2, 2016 for U.S. Appl. No. 14/286,793.
"Point Cloud," Sep. 10, 2010, Wikipedia.
Racadio et al., "Live 3D guidance in the interventional radiology suite," Dec. 2007, AJR, 189:W357-W364.
Solheim et al., "Navigated resection of giant intracranial meningiomas based on intraoperative 3D ultrasound," May 14, 2009, Acta Neurochir, 151:1143-1151.

\* cited by examiner

Sensed, Predicted, and Displayed Vectors $\mathcal{F}_h$: Inputs from User $\mathcal{P}_d$: Display Position Data $i_{mi}$: Image Data $i_{mo}$: Image Output $i_a$: Image of Anatomy $S$: Input Device Command $\mathcal{P}$: Parameter Values

SYSTEM AND METHOD FOR VIRTUALLY TRACKING A SURGICAL TOOL ON A MOVABLE DISPLAY

CROSS-REFERENCE

This application claims the benefit of U.S. Provisional Application No. 61/535,753, filed Sep. 16, 2011; U.S. Provisional Application No. 61/585,580 filed on Jan. 11, 2012; and U.S. Provisional Application No. 61/615,141 filed on Mar. 23, 2012, all of which are incorporated herein by reference in their entirety.

BACKGROUND OF THE INVENTION

1. Field of the Invention

The invention relates generally to the diagnosis and treatment of disorders using minimally invasive techniques. In many minimally invasive procedures very small devices are manipulated within the patient's body under visualization from a live imaging source like ultrasound, fluoroscopy, or endoscopy. Live imaging in a minimally invasive procedure may be supplemented or replaced by displaying the position of a sensored medical device within a stored image of the patient anatomy.

Many minimally invasive catheter procedures are conducted in expensive hospital settings by specialized physicians. Often small, percutaneous medical devices are visualized during the procedure by using live fluoroscopic imaging. While the fluoroscopic imaging provides a live image of fluoro-opaque devices, it has many drawbacks:

Time spent in a fluoroscopy suite is very expensive and raises the cost of many minimally invasive medical procedures.

Ionizing radiation used to create the fluoroscopic image is dangerous to the patient, physician, and assistants.

The fluoroscopic image is a two-dimensional projection which does not provide determinant information about motion of the medical device towards or away from the fluoroscopic image collector During a typical minimally invasive procedure the physician must look away from the patient and his or her hands to see the display showing the fluoroscopic image. Additionally, the frame of reference for the fluoroscopic image is typically misaligned from the frames of reference for the physician, the tool and the patient. This presents a challenging situation for the physician who must compensate for differences in these frames of reference. For instance, when the physician inserts a device into the patient by moving his hands from left to right, the fluoroscopic image of the device moves towards the top of the display. The physician must compensate for the misalignment of the coordinate systems for the respective frames of references while also concentrating on achieving the goals of the minimally invasive procedure. All the while the physician's need to look away from the patient and his or her instrument creates an ergonomic challenge in addition to this mental challenge. As a result the completion of minimally invasive procedures becomes delayed increasing the procedure cost and the exposure of the patient and surgical team to ionizing radiation.

Prior to a minimally invasive catheter procedure, patients often have an anatomical image created using CT or MR imaging systems commercially provided by companies like Philips, Siemens, General Electric, and Toshiba. The anatomical images can be processed, or "segmented," into three-dimensional representations of the anatomy of interest. Individual organs, muscles and vasculature can be visually separated from other anatomy for even clearer viewing of regions of interest. In this invention the three-dimensional pre-procedure images may be used instead of fluoroscopy for navigation during the procedure because the position and orientation of the medical device can be sensed in real-time. For example, navigation systems provided by Medtronic, GE, and Stryker sense the positions of medical devices within the patient's body and present the sensed position data in a pre-procedural image of the patient's anatomy. These navigation systems provide a supplement or replacement to fluoroscopic imaging so that the physician may conduct a minimally invasive procedure within the patient's body using little or no X-ray. However, the navigation systems do not provide a means for making the physician's hand motions on the medical device match the motions of the device displayed in the image of the anatomy on the display. In order to make minimally invasive procedures easy and intuitive, the coordinate systems of the patient, the device, the display, and the physician's hands must be unified.

Minimally invasive procedures where the medical device follows the natural paths of internal anatomical conduits are especially well suited for a system that provides navigation assistance by unifying the physician, patient, display, and device coordinate systems. These procedures usually employ very small devices that are internally navigated through very small anatomical conduits. For example, to treat uterine fibroid tumors, a physician inserts a small 5 F (0.065") catheter through the femoral artery into the internal iliac artery and then advances a 3 F (0.039") catheter into the uterine artery. In this procedure, the arteries that provide a conduit for the medical devices are often only 1-2 mm (0.039-0.078") in diameter and a small error in navigation may result in the physician being unable to reliably choose the correct pathway. Similarly, to treat drug-refractory hypertension, a physician may insert a 6 F ablation catheter through the femoral artery to the aorta and into the renal artery under live fluoroscopic imaging. If live X-ray were not needed, the renal ablation procedure could be done more quickly and less expensively.

The present invention minimizes the exposure of the patient to ionizing radiation and improves the ease and reliability of navigating a minimally invasive device within a patient by providing a system for displaying the device and patient anatomy in a substantially aligned manner.

SUMMARY OF THE INVENTION

The invention comprises a virtual window system that creates a visual coherency between the image of the patient and his or her anatomy and the patient by aligning the image of the patient anatomy on the display to the patient and presenting the image to the user that feels is if the user is looking directly into the patient through the display. The invention is designed to also display medical devices, such as a minimally invasive tool. The invention makes the anatomy and the motion of the minimally invasive medical device in the display match the motion of the physician's hands by substantially unifying the coordinate systems of the patient, the medical device, the display, and the physician's hands. The invention creates a visual coherency between the motion of the medical device in the image and the motion of the physician's hands manipulating the device. This invention also creates a visual coherency between the motion of the image in the display and display.

Embodiments of the invention possess inventive design elements that improve the ergonomics and increase the workspace of the virtual window surgical system. Furthermore, coupling the position and orientation of the display to the image allows the image to remain aligned to the patient for various positions and orientations of the display. To improve the workspace of the system, this invention allows for decoupling the relationship to reposition the display independently of the image. For instance, an aligned display may interfere with other equipment during some portion of the procedure and it may be desirable to un-align and reposition the display slightly to relieve the interference. Additionally this invention allows for a scaled coupling for improved ergonomics. For instance, moving the display with a unity ratio may cause the display to interfere with other equipment during some portion of the procedure or may make the screen difficult to view. A 1.5:1 scale would increase the ergonomics of the system while maintaining the visual coherency between the patient and the image. It should be noted that the display may be repositioned along multiple axes and in multiple directions and that the scaling may be different for different axes and directions. Additionally this invention provides a movable support structure to place a display directly in front of the physician, in between the physician and the patient. Ideally the images are presented in a fashion such that the images are substantially aligned with the patient. This invention details the methods and techniques needed to align the images to the patient. Many embodiments utilize a display that is mounted on a movable support structure that allows for the display to be positioned between the patient and the physician. The range of motion of the support structure and the degrees of freedom enable a wide range of display positions and orientations. In one embodiment, the patient is lying on a surgical table with the physician standing by the patient's side. The support structure allows the display to be brought over the patient. The physician can move and orient the display so the display is located roughly between him/her and the patient. This improves the ergonomics of the surgical workspace by allowing the physician's general gaze to remain in the same spot throughout the procedure, without having to look up to a display located away from the surgical site.

Furthermore, techniques are disclosed to track the position of the display, the imaging source, the patient, and the table. Tracking individual elements of the system allows the image to be aligned with the patient and constantly updated to accommodate for a moving patient, moving table, moving imaging source, or moving display.

Specific embodiments of the display support structure are also disclosed. The support structures described allow for maximum versatility and usability.

Unifying the position of the display image and the patient anatomy makes the physician's control of a medical device within the anatomical image substantially coordinated, ultimately resulting in faster, easier, and more precise medical procedures. Additionally, this invention provides for a switch to decouple the relationship between the display position and orientation and the image position and orientation. This allows the user to move the display to a new position without affecting the image. This may be desirable if the display itself is interfering with some portion of the procedure, like the imaging source itself, and a different position would be more desirable. This invention also allows for the relationship between the display position and orientation and the image position and orientation to be scaled. A scaled relationship of greater than one would cause the image to move more than the display. A 1.5:1 ratio is preferred to increase the ergonomics of the system while maintaining the perception of a virtual window.

In a second embodiment, a live image of the patient anatomy is displayed on a display located over the patient. Sensors track the position and orientation of the display screen and the imaging source so that the position and orientation of the display screen may control position and orientation of the imaging source, to keep the anatomical image, the medical device image, and the patient substantially co-aligned. Alternatively, sensors track the position and orientation of the display screen and the imaging source so that the position and orientation of the imaging source may control position and orientation of the display screen, to keep the anatomical image, the display screen, the medical device image, and the patient substantially co-aligned. The live image may be supplemented with other anatomical images from live or static sources that are sensored, registered, and displayed in the same substantially co-aligned manner on the display screen.

Each of these embodiments creates a coupling between the image position and orientation and the position and orientation of a secondary system component. This invention improves the workspace of the system by providing an input device to temporarily decouple the relationship to reposition the display or secondary system component for improved workspace. Additionally, this invention improves the ergonomics by allowing for a scaling factor between the coupled display and secondary system component.

In another embodiment the system comprises a processor further adapted to receive image data for the patient's anatomy. Such image data may be a static image obtained by MRI, ultrasound, X-ray, computed tomography or fluoroscopic imaging modalities. The image data can also be a live fluoroscopic image collected in real-time. The system can further track patient position by one or more of the following fiducials, live imaging data, external optical sensors, or electromagnetic sensors. The processor is also further adapted to receive position data from a tool, which is tracked by electromagnetic sensors. The display is held by a support arm having at least 1 degree of freedom, wherein the members and joints of the support arm may be operatively coupled to counterbalance springs or weights. The processor is further adapted to receive position data of the display, which is tracked by one or more of the following: external optical tracking, electromagnetic sensors, or encoded joints of the support arm. The processor processes the various position data and image data to display an image of the patient's anatomy substantially aligned with the patient's actual anatomy superimposed with the position of any tool being tracked. The processor is also adapted to direct any live imaging equipment to ensure proper functioning of the system. When used in a surgical setting the invention may be located in the surgical field and may also comprise a sterile drape for the display to protect the integrity of the surgical field.

In one embodiment, a live image of the patient anatomy is shown on a repositionable display screen located over the patient. The physician can move the display over the patient while sensors track the motion of the display so that the image shown on the display screen may be periodically or constantly updated to show the medical device, and the patient anatomy substantially aligned with the patient from the perspective of the user. In this manner, the image shown on the display provides a view of the medical device and patient anatomy that is intuitive and allows for easy navigation of the medical device within the patient anatomy shown on the display screen. While the image of the anatomy is frequently based on a pre-operative image, a live image may be supplemented with other anatomical images from live or static sources which are sensored, registered, and displayed in the same substantially co-aligned manner on the display screen.

In additional embodiments, a sensor on the medical device provides position and orientation data of the device to a data processor. A sensor on the patient provides position and orientation data of the patient to the processor, and sensors on the display screen provide the viewing position and orientation of the display screen to the processor. With data from the medical device, the patient, and the display, the processor unifies the three coordinate systems so that the image shown on the display screen substantially matches the position of the patient anatomy. Adjustments to the display position over the patient result in similar changes to the position of the image in the display: changing the position of the display changes the view of the image on the display screen. For example, the user may change the angle of the display to change the angle of the apparent image on the display screen or may translate the display to pan the image in the display along the patient to show different anatomy. Aligning the positions of the shown image and the patient anatomy helps coordinate the physician's control of the medical device.

Elements of both embodiments may be combined to display preoperative and intra-operative anatomical images within the same procedure. In both embodiments, the invention provides a virtual window into the patient where the physician may view the anatomy and navigate the surgical device in substantial alignment with the patient.

In a first aspect of the present invention, a system for displaying an image for the tool on an image of a patient on a moveable display comprises a display screen and a processor. The display screen is configures to be moved and aligned with the target region on an exterior of a patient's body, and the processor is configured to receive data representing the patient's, data representing a position of a tool introduced to the patient's body in real time, and data representing a position of the display screen in real time. The processor is configured to deliver to the display an image of the patient anatomy having an image of the tool superimposed thereon. A position of the image of the tool on the image of the anatomy is updated in real time, and a target region of the anatomy which is presented as a virtual image on the display is selected by moving the display screen relative to the region and the patient body. The system can be used in performing methods for displaying the image of the tool on the patient image as described in more detail below.

In specific embodiments of the systems of the present invention, the system further comprises an external tracker for tracking a position of the tool in the patient's body, where the tracker generates the data delivered to the processor. For example, the tracker can be configured to track an electromagnetic sensor on the tool, as described in more detail below.

In further specific aspects of the systems of the present invention, the system may comprise a support for moveably holding the display screen relative to the patient's body. The support may, for example, may comprise an articulated arm, and the support may optionally be encoded to produce the data representing the position of the display screen which is sent to the processor.

In further specific embodiments, the system may further comprise an external tracker for tracking the screen to produce data representing a position of the display screen. The external tracker may be configured to track an electromagnetic sensor on the screen, and in many embodiments may be the same external tracker which is used for tracking the position of the tool and optionally for tracking the position of the patient body as described in more detail below. External trackers used in the present invention may also rely on other tracking technologies, including acoustic signals, optical sensors, encoders, fiducial markers, patient patches, and the like.

The patient anatomy data may be derived from a variety of conventional patient imaging methodologies, including x-rays, fluoroscopy, CT scanning, MRI, ultrasound, and the like. The images are converted to a data stream which is delivered to the processor, and the images may be static or delivered in real time. By "static image," is meant that in pre-operative images obtain of the target regions in the patient body and the image used then to allow the processor to display selected target regions from the larger anatomy which has been imaged. Real time images will be obtained using an imaging device which is located adjacent the patient and which is typically repositioned to align the image with the target anatomy. This will be discussed in greater detail below. Movement and positioning of the imaging device may be controlled through the imaging screen.

In further specific embodiments of the systems of the present invention, an external track is configured to track movement of the patient's body, where the processor is further configured to receive data from the tracker representing the position of the patient's body. The processor adjusts the position of the patient anatomy which is presented on the display screen in response to the body movements in real time, thus assuring that the images of the patient anatomy and the tool remain properly registered with the patient's body over time. As noted above, this external tracker may be in addition to one or more other external trackers or may be combined in a single external tracker for tracking the display screen and the tool.

In a second aspect of the present invention, the methods for displaying an image of a tool on an image of a patient on a moveable display screen comprise aligning the display screen with a region of the patient's body approximate a target anatomy of the patient. An image of the target anatomy is displayed on the display screen, and an image of a tool is superimposed on the image of the target anatomy. The position of the tool image corresponds to a position of an actual tool in or on the actual patient anatomy. The position of the tool image on the anatomy image is updated in real time as the position of the actual tool changes relative to the actual patient anatomy. A region of the anatomy which is presented on the display screen can be changed by moving the display screen relative to the region of the anatomy and the patient. In this way, the user can track the position of the actual tool in real time on an image of the patient anatomy as the tool is being advanced, deployed, or otherwise positioned or repositioned within the actual patient anatomy.

Displaying the image of the target anatomy may comprise either displaying a pre-operative static image, displaying a real-time image obtained by an imaging device, or some combination of the two. Position data of the tool in real time is typically obtained by tracking the tool in the actual patient anatomy using an external tracker, such as those described above. A position of the display screen is also tracked, typically using an external tracker as described above, and the changes in position are used to update the images to presented on the display screen. Additionally, a position of the patient's actual anatomy may be monitored and further used to shift the coordinates system upon which the anatomy and the tool images are presented in response to changes in patient and actual anatomy positions.

In a third aspect of the present invention, a system for displaying an image of a patient anatomy on a moveable display comprises a display screen, a processor, and means on the display screen allowing a user to adjust a spatial relationship between the position of the display screen and an image of patient anatomy represented on the display screen. The processor is typically configured to receive data representing the patient's anatomy and data representing a position of the display screen in real time. The processor is typically further configured to deliver to the display screen an image of the patient anatomy to which changes in real time in response to movement of the display screen in accordance with a spatial relationship between a position of the patient's actual anatomy and the position of the display screen in real time.

The display screen means optionally allows a user to selectively interrupt the spatial relationship so that the image of the patient's anatomy remains unchanged while the display screen is moved and to thereafter resume the spatial relationship (tracking) so that the image of the patient's anatomy can resume moving and being updated on the display screen.

Alternatively or additionally, the display screen means can allow a user to adjust the scale of the spatial relationship so that movement of the display screen through a particular distance results in a corresponding movement of the image on the anatomy over a different apparent distance. The apparent distance on the display screen may be greater than or less than that of the actual movement.

The display screen means more typically comprise a tracking feature on the display screen itself, but could in other instances be on the processor, be on a separate controller (such as a footswitch), or the like. When on the display screen, the tracking feature may comprise any one of a tracking pad, a roller ball, a joy stick, or the like. Alternatively, the tracking feature could be implemented on a touch screen which may be the display screen itself. As a still further alternative, the tracking feature could be voice-activated.

Other features of the system of the third aspect of the present invention have been described previously with respect to the first system above.

In a fourth aspect of the present invention, a method for displaying a patient image on a moveable display comprises aligning the display screen with a region of the patient's body approximate a target anatomy of the patient. An image of the target anatomy is displayed on the display screen where the image of the target anatomy has a spatial relationship between a position of the patient's actual anatomy and the position of the display screen in real time. As the display screen is moved relative to the actual anatomy, the spatial relationship may be adjusted in real time so that at least one of a scale of the spatial relationship or continuity of the spatial relationship is changed. The continuity may be changed by interrupting a spatial relationship so that the display screen can be moved without moving the image of the patient anatomy on the display screen. The relationship may be resumed later. The spatial relationship may be modified when interrupted such that upon resumption of the spatial relationship any changes in the position and orientation of the display made during the interrupted state are not used by the modified spatial relationship and do not affect the image delivered by the processor (using the spatial relationship) to the display. The movement of the image can then be resumed on the display screen has assumed a different spatial relationship (either in or out of alignment with the target region) with respect to the patient. Changing the scale of the spatial relationship adjusts the magnitude of movement of the image on the display screen relative to the magnitude of the actual distance that the display screen is moved relative to the patient. The scale can be selected so that the movements are on a 1:1 scale, or any other scale which is greater or less than a 1:1 scale.

Further aspects of the methods of the fourth aspect of the present invention have been described above with respect to the methods of the second aspect of the present invention.

In a fifth aspect of the present invention, systems for displaying an image from a repositionable patient imaging device on a moveable display comprise a display screen, a repositionable imaging device, and a processor. The display screen is configured to be moved and aligned with target regions on an exterior of a patient's body. The repositionable imaging device is configured to be moved and aligned with target regions on an exterior of a patient's body. The processor is configured to coordinate movement of the display screen and of the repositionable imaging device so that the display screen is positioned in a desired relationship with the target region which is being imaged by the repositionable imaging device.

In a specific embodiment of the system, the processor may be configured to reposition the imaging device in response to movement of the display screen. In an alternative embodiment, the processor may be configured to move the display screen in response to repositioning of the device.

Other specific aspects of the fifth aspect of the present invention have been described previously with respect to the earlier described systems.

In a sixth aspect of the present invention, methods for displaying an image from a repositionable patient imaging device on a moveable display screen comprise repositioning the imaging device and moving the display screen. As the imaging device is repositioned to image different target regions on a patient's body. The display screen is moved to position the screen in a desired relationship with the target region being imaged by the imaging device. Repositioning of the imaging device and moving the display screen are coupled so that (1) repositioning the imaging device causes the display screen to move to maintain the desire relationship or (2) moving the display screen causes the imaging device to reposition to maintain the desired relationship.

In specific aspects of this method, movement of the display screen and repositioning of the imaging device may be scaled or the scale can be 1:1 or may be other than 1:1. Typically, means are provided on the screen for adjusting such scaling, although means could be provided on the processor, or other places, or may be voice-activated in order to adjust such scaling.

In any aspect of the present invention as described previously the display screen, patient, support arm or any live imaging sources may be equipped with sensors to produce position data of the display screen, patient, support arm, or live imaging source.

Other features of the sixth aspect of the present invention has been described previously with earlier aspects.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Figure 1:
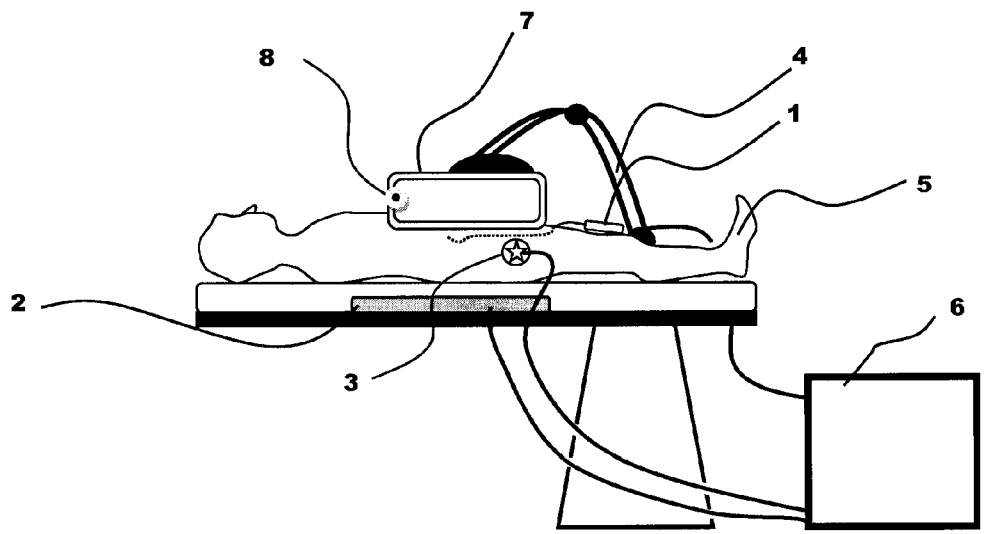
FIG. 1 is a side diagrammatic view of a system for displaying a substantially co-aligned anatomical image with a sensored medical device over a patient's anatomy.
Figure 2:
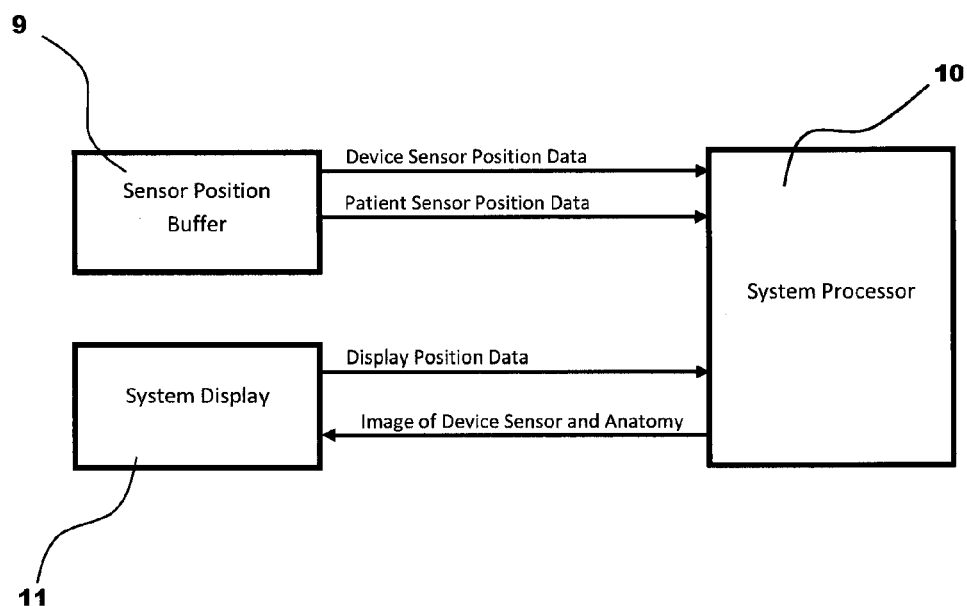
FIG. 2 is a block diagram showing data flow for the system in FIG. 1.

FIGS. 1-2 describe an embodiment for navigating a minimally invasive medical device within the patient using an acquired three-dimensional anatomical image shown in a display 7 that is substantially aligned to the patient anatomy. A sterile cover may be used to separate the display from the sterile operating field and the sterile cover may incorporate a conductive film to provide a sterile touch interface for a capacitive touch screen display. The sterile display cover may be a flexible, clear drape made of plastic like polyethylene or polyurethane film, a rigid plate made of clear plastic like polycarbonate or acrylic, or a combination of both flexible and rigid plastics. The display is preferably a light-weight, flat LCD display provided by manufacturers like LG Display, Philips, and Innolux or a light-weight, flat OLED display provided by manufacturers like Samsung and Sony. A prime example of such a display would be the NEC TFT color LCD module which provides a usable viewing angle of 85° in all directions. In FIG. 1, the position of the medical device within the patient 5 is provided by an electromagnetic coil sensor located on the distal elongated section of the medical device 1. The position of the sensor is derived through an electromagnetic transmitter 2 similar to those transmitters supplied commercially by NDI and Ascension Technology Corporation. Alternatively, the position of the medical device may be derived from an optical fiber position sensor like that supplied by Luna Innovations. A similar patient reference sensor 3 is placed on the patient in a reliably stable position like the outcropping of the pelvic bone, sternum or clavicle. The reference sensor or sensors provide frequently updated data describing the position of the patient anatomy in the same coordinate system as the medical device sensor. The patch holding the patient sensor may be placed on the patient before the patient's anatomy of interest is imaged and the patch may contain known X-ray visible materials such as tungsten, platinum-iridium, platinum, barium sulfide or iodine and MR visible materials such as gadolinium or vitamin E. The patch is visible within the image of the anatomy and therefore the patient reference sensor 3 can be registered to the three dimensional anatomical image. Position data from the sensor in the medical device 1 and patient reference sensor 3 and display support arm 4 are sent to the system processor 6. The local coordinate systems of the medical device sensor 1 and display 7 may undergo a coordinate system transformation in the system processor so that the positions of the device sensor, patient sensor, and display may be evaluated in a single world coordinate system. Display 7 has a user input button 8. FIG. 2 shows the flow of sensor position data from the sensor buffer 9 to the system processor 10 where the position sensor data is used by the processor to place an icon of the medical device into the three-dimensional patient anatomy image for display through the system display 11. The system processor is a standard computing system like those supplied by Dell or Hewlett Packard running an operating system like Windows or Linux. Position data from the system display and support arm is likewise used by the system processor to orient the image on the screen so that the image, based on display position data from the display 7 and support arm 4 and patient position data from the patient reference sensor 3, is substantially aligned with the patient anatomy. Display position data may also be used to modify the image in the display, for example zooming or clipping the image as the display moves closer to the patient. Other image modifications may include changing transparency, removing layers, removing anatomical structures, or changing colors. Additionally, scaling of the image in discrete steps or image modifications may be done via a touch sensitive surface on the display.

Figure 3:
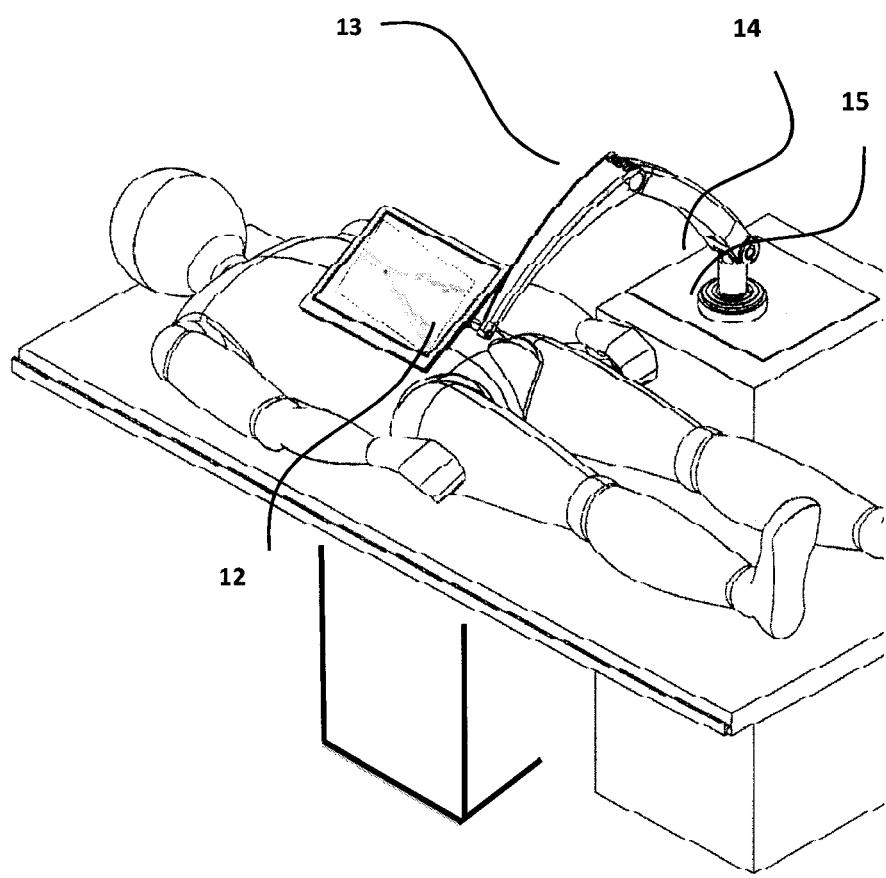
FIG. 3 is an isometric view of an embodiment of the display and support arm positioned next to the patient table.

FIG. 3 presents an embodiment of the display and support arm with passively counterbalanced joints at the support arm elbow 13, and shoulder 14. An additional rotational or linear joint is provided at the base of the shoulder 15 to allow the display to move along the inferior to superior axis of the patient. All support arm joints may be encoded to provide data describing the position of the display. The display support is shown in an embodiment where the arm is mounted to a portable cart that is positioned next to the patient table. Axis 12 allows the display to rotate. An alternate embodiment may attach to the table or imaging system.

Figure 4:
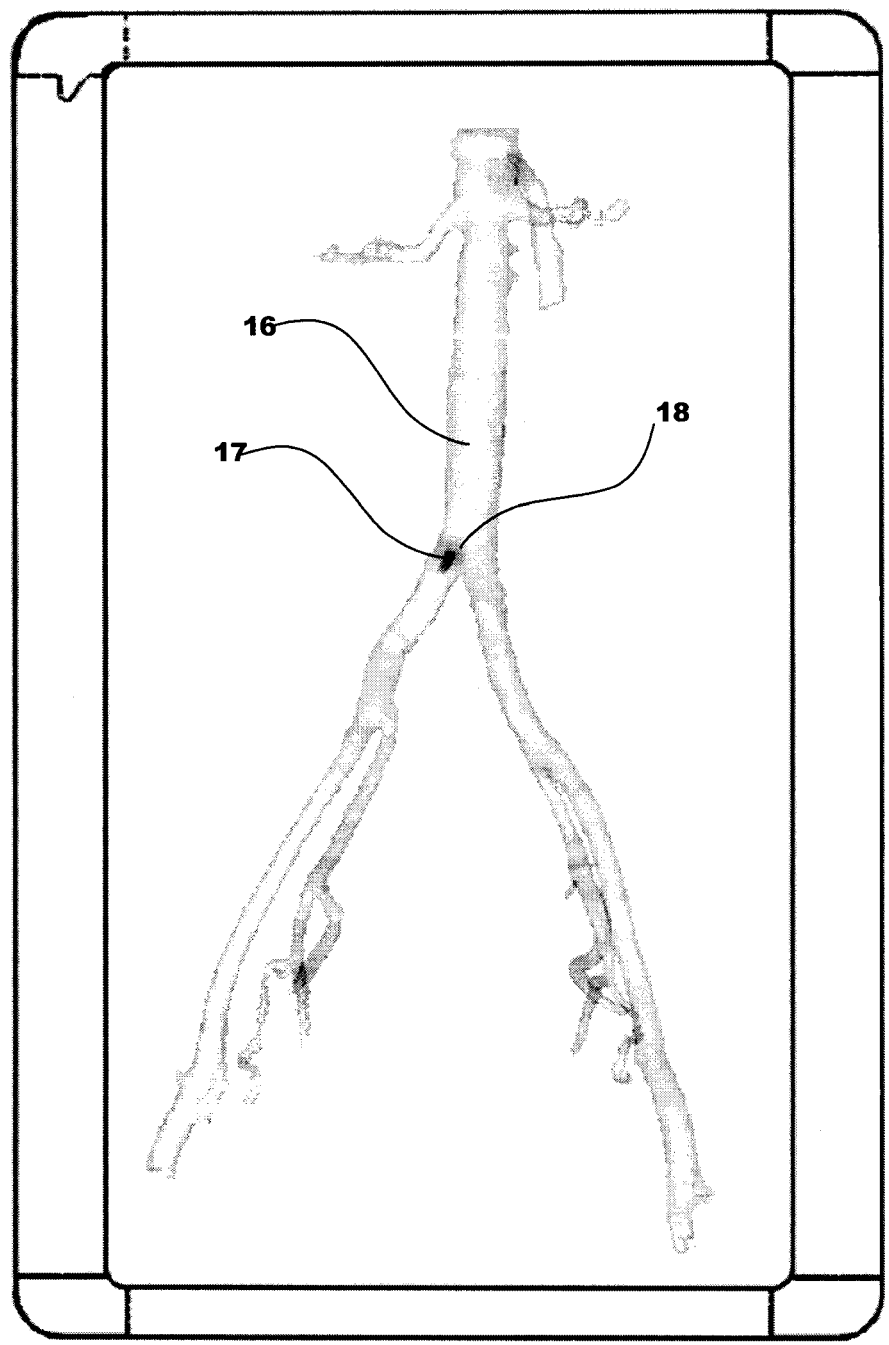
FIG. 4 is a plan view of the display with a three-dimensional segmented anatomic image and an icon showing the position of the sensored medical device.

FIG. 4 shows a close-up image of an embodiment of the display with three-dimensional vascular anatomy 16 presented on the display. An icon, representing the location the position sensor of the catheter 17 is shown within the three-dimensional anatomical image along with a semi-transparent spherical icon 18 showing the accuracy of the positional data for the catheter position is displayed.

Figure 5:
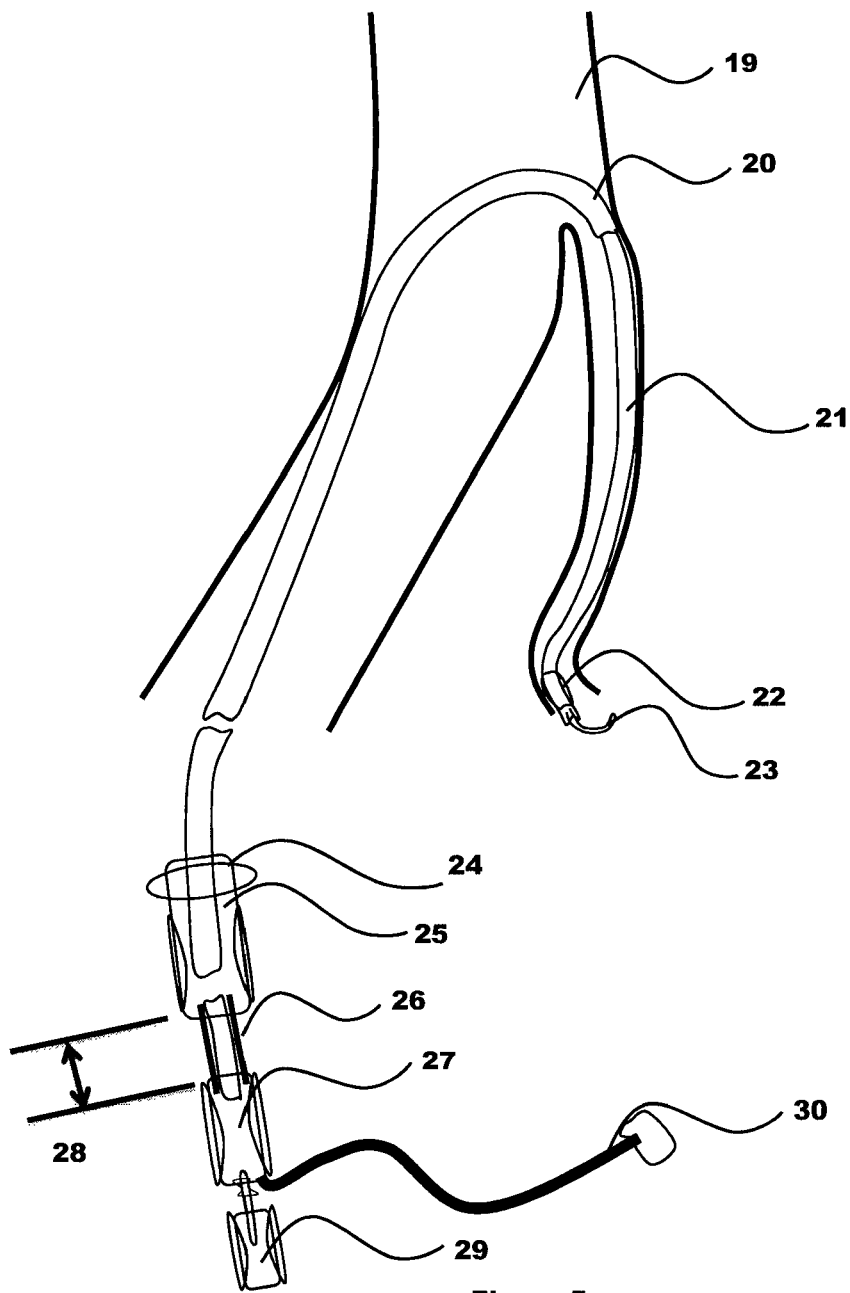
FIG. 5 is a diagram of a percutaneously delivered minimally invasive sensored medical device within an anatomical conduit.
Figure 6:
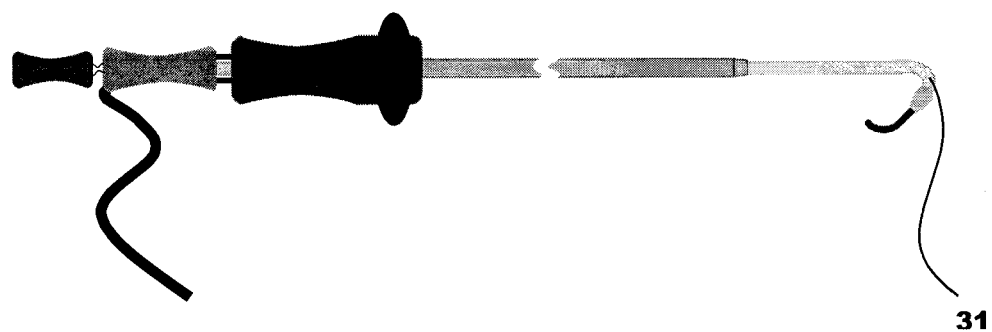
FIG. 6 is two plan view diagrams of the sensored percutaneous medical device.
Figure 6:
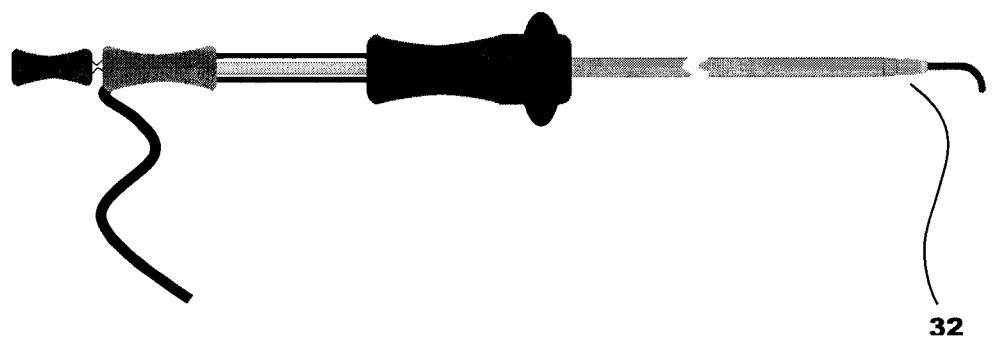

A preferred embodiment of the sensored medical device is shown in FIGS. 5-6. The medical device is shown in a section of a blood vessel 19 with the distal articulating section 20 of the outer elongated tube, manually controlled by an internal pull-wire tensioning 24 lever on the handle 25, curved to cannulate a branch of the vessel. The inner elongated tube 21 is extended to cannulate the distal branch of the vessel. A five degree-of-freedom single coil sensor 22 is wrapped and covered on the distal external section of the inner elongated tube. An integrated guide-wire 23 may be extended through the internal lumen of the medical device or may be removed with the guide-wire handle 29 so that therapeutic and diagnostic agents may be delivered. The linear extension guides 26 between the handle 25 of the external elongated tube and in the handle 27 of the internal elongated tube may be used to limit and measure extension 28 of the internal elongated tube. Extension measurements may be performed with commercially available sensors like optical encoders, potentiometers, or LVDTs. A similar rotation limit and measurement sensor may be incorporated into the device handle to limit and measure rotation between the device handles. Data from the distal device sensor 22 and from the handle rotation and extension sensors are transmitted to the system processor through the sterile data transmission cabling 30. FIG. 6 provides additional views of the medical device with the internal elongated tube shown extended and curved 31, and retracted 32.

Figure 7:
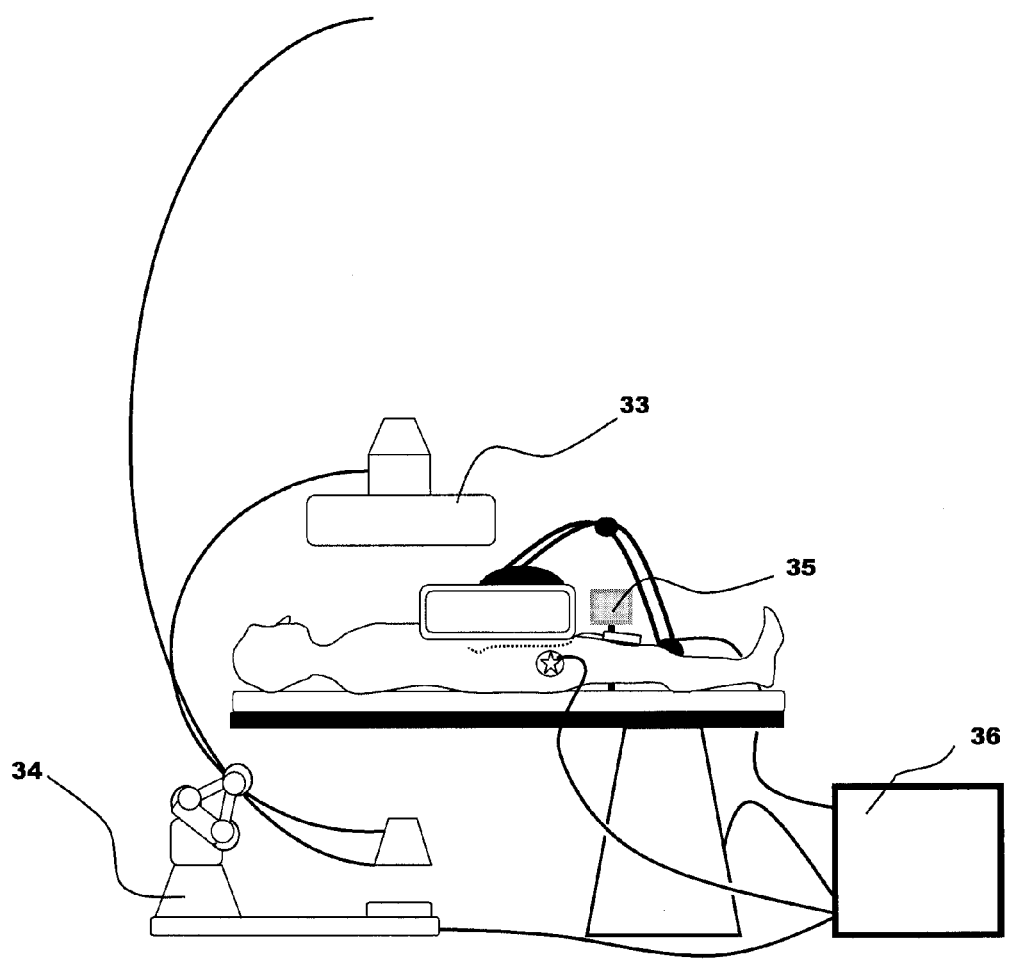
FIG. 7 is a side diagrammatic view of a system for displaying a substantially co-aligned anatomical image with a sensored medical device and a live fluoroscopic imaging source over a patient's anatomy.
Figure 8:
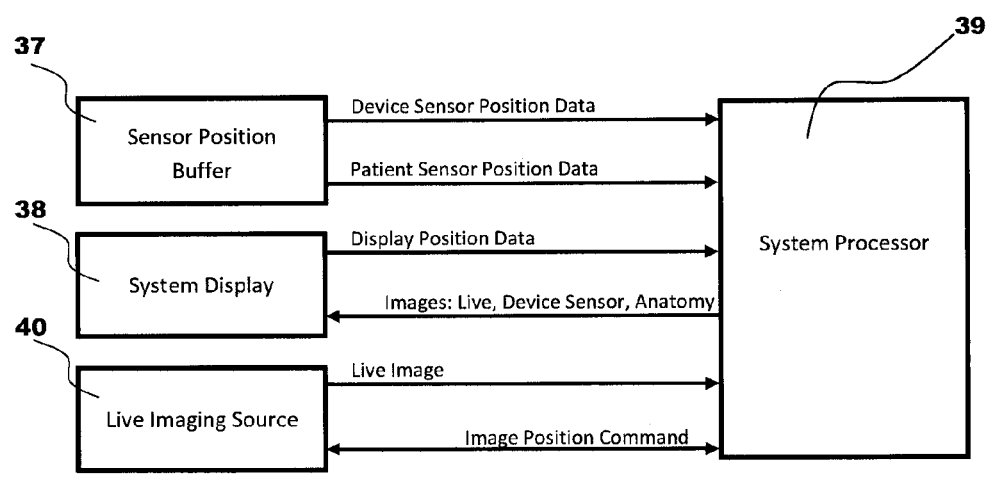
FIG. 8 is a block diagram showing data flow for the system in FIG. 7.

FIGS. 7-8 detail an embodiment for navigating a minimally invasive medical device within patient using an acquired three-dimensional anatomical image in conjunction with a live image. Both live and acquired anatomical images are shown in a display that is substantially aligned to the patient anatomy. In FIG. 7, a live image is provided by a fluoroscopic imaging system 33 and the live fluoroscopic image is sent to the system processor 36. A remote electromagnetic transmitter 35, such as those commercially available from Northern Digital Incorporated (NDI) and Ascension Technology Corporation, is positioned outside the fluoroscopic image field to localize sensors on at least the medical device. As the display is repositioned to provide the optimum view for navigation of the medical device within the anatomical image, the acquired image is repositioned in the display to remain substantially aligned with the patient anatomy. Likewise, the live image is modified as the system processor 36 sends a command to the fluoroscopic positioning arm 34 so that the live image in the display remains aligned to the acquired image and substantially aligned to the patient anatomy. FIG. 8 shows the data flow from the sensors 37 on the patient and in the medical device to the system processor 39. The system processor 39 collects the patient and device sensor data and the live image 40, performs coordinate system transforms to unify the patient, image, and sensor coordinate systems, and presents the images of medical device and anatomy in the system display 38.

Figure 9:
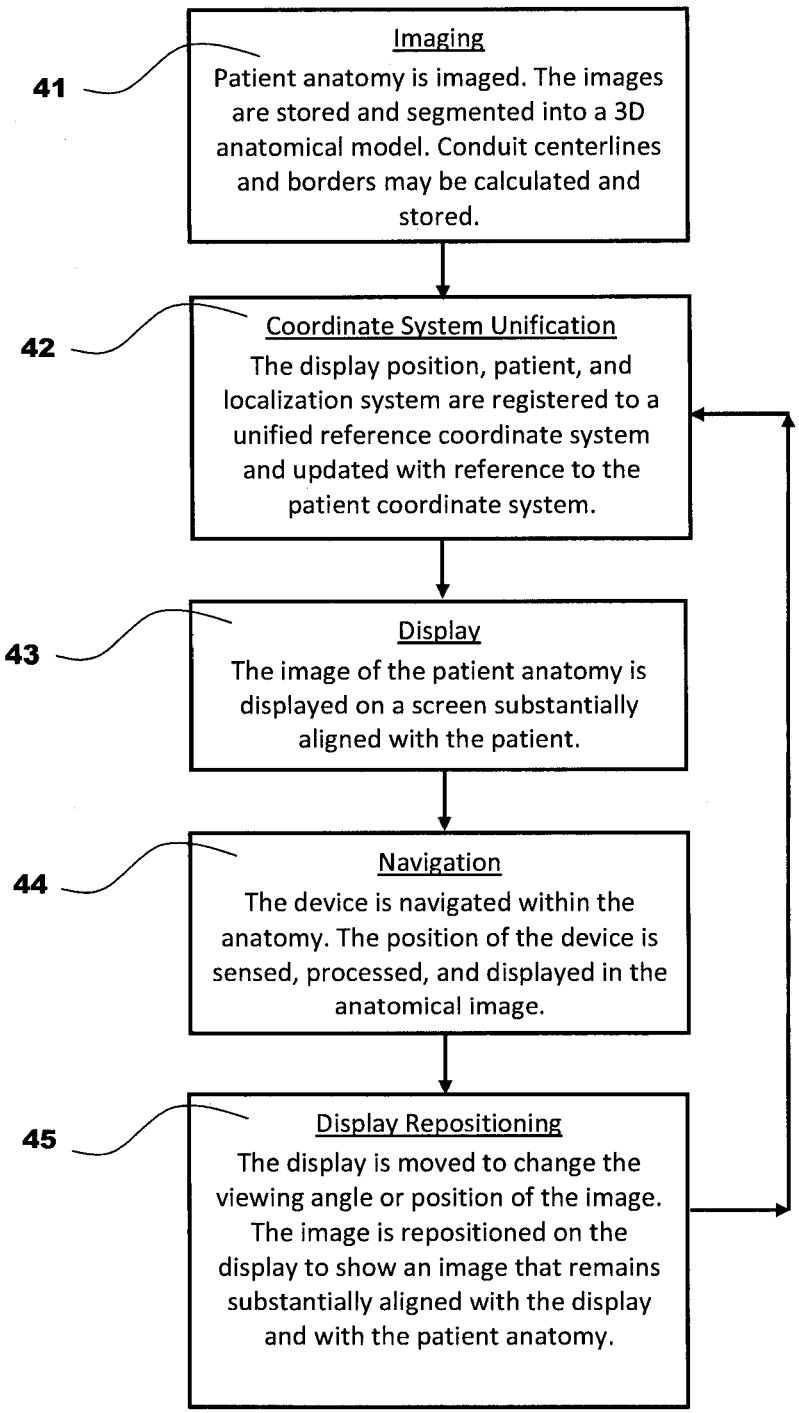
FIG. 9 is a flow chart describing the basic steps for a minimally invasive procedure using a sensored medical device and the system for displaying a co-aligned image.

FIG. 9 provides an overview of the procedure flow for a minimally invasive procedure using a stored image for navigation. The patient anatomy is imaged 41 with a non-invasive imaging modality like CT, MR, or rotational angiography. The imaged anatomy is stored and segmented into a three dimensional image, and borders and centerlines of vessels and conduits are calculated using commercially available software from vendors like Philips, Siemens, GE, Toshiba, Materialise, or Osirix. The image is transferred to the memory of the system processor and the image is registered 42 to the system coordinate system along with the patient and the medical device sensors. Registration of the image may be done by imaging the patient with an image-visible skin patch or with an externally anatomical marker placed on the patient. At least three separate points of the patch are visible in the image and then a position sensor is placed into the patch. The visible points on the patch may be selected on the displayed image and then the known distance from the visible patch fiducials is used to register the image to the patient position sensor. The patient position sensor and medical device position sensor are inherently registered because their positions are determined by the same sensing system. Next, the registered image is shown 43 above the patient in a manner substantially aligned to the patient anatomy. The medical device may be navigated 44 within the patient as the position sensor in the medical device is tracked and presented as an image icon within the image of the patient anatomy. The image of the anatomy and the image of the medical device may be shown with varying degrees of transparency to maximize the visibility of the device and anatomical images. The display, showing the image of the medical device within the image of the anatomy, may be repositioned 45 to enhance the viewing angle of the anatomy. As the display is moved, the image on the screen is updated to maintain substantial alignment between the displayed anatomical image and the patient anatomy.

Figure 10:
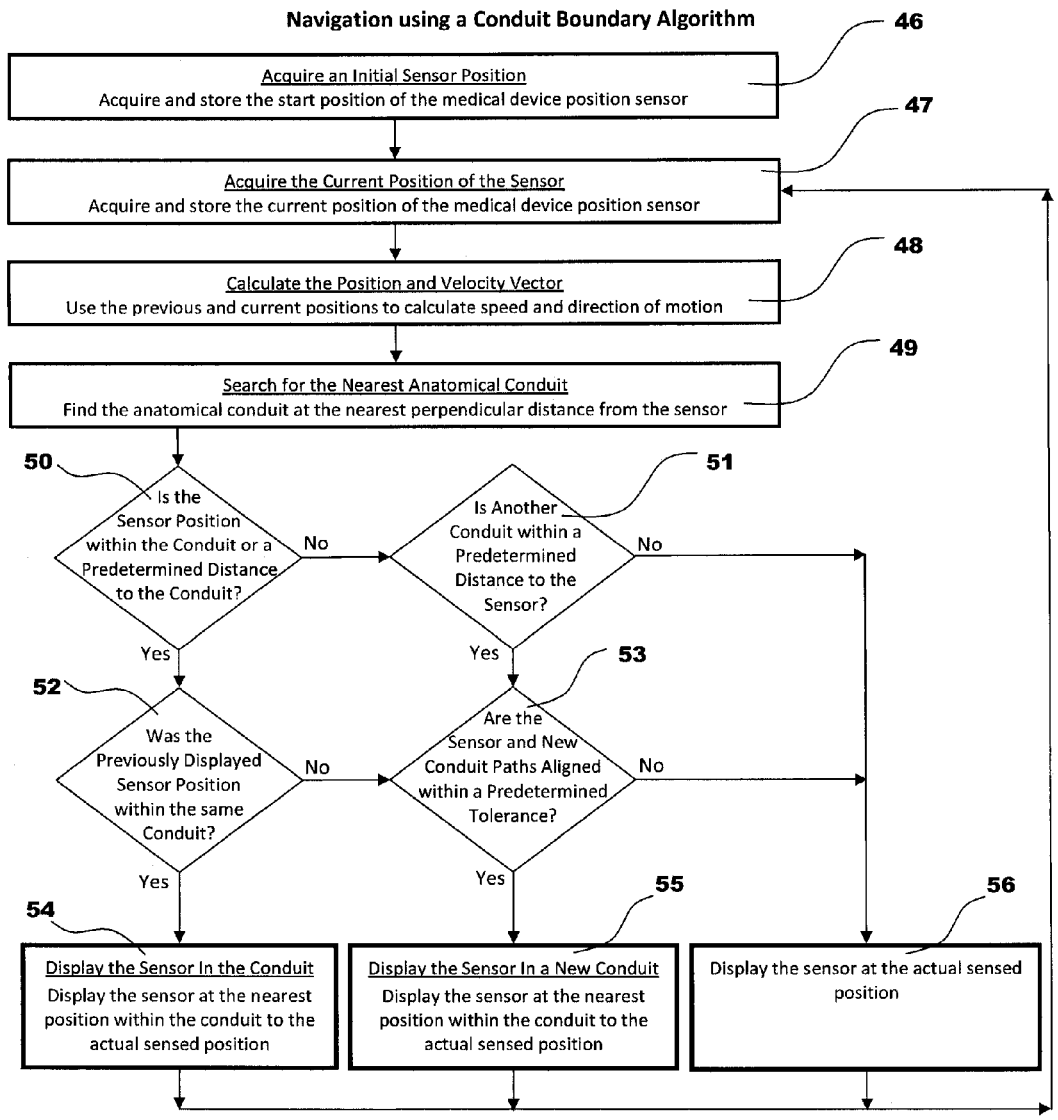
FIG. 10 is a flow chart describing an algorithm for displaying the icon of the sensored medical device within the conduits of the anatomical image.
Figure 11:
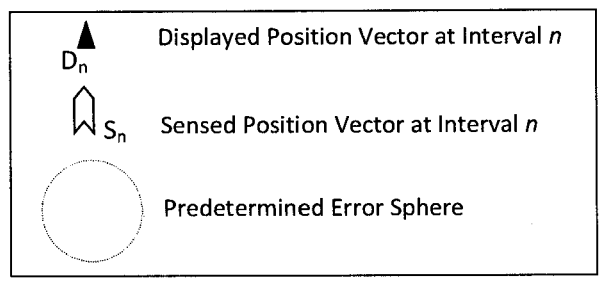
FIG. 11 is a stepwise diagram of the potential results of the flowchart of FIG. 10.
Figure 11:
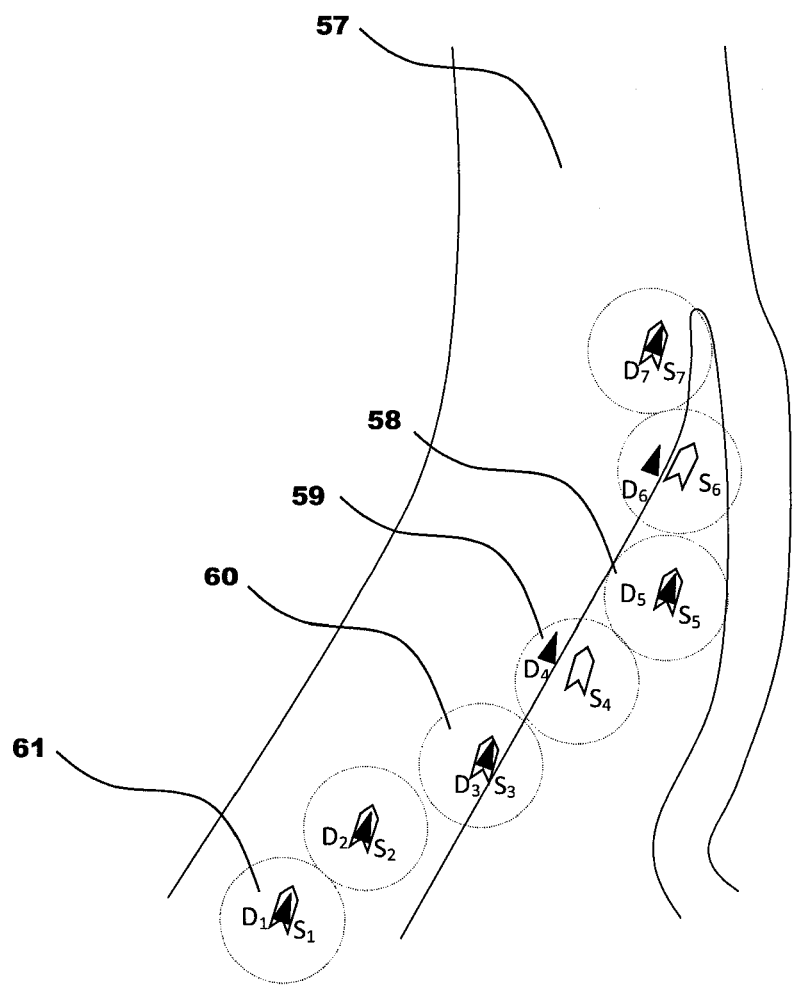

FIGS. 10-11 describe specific algorithmic details of an embodiment for displaying a sensed medical device within images of anatomical conduits like blood vessels. The embodied medical device navigation system may be thought of like a GPS navigation system used in a car: a vehicle (the medical device) is shown on a map (the anatomical image) and is usually constrained to roads on the map (the conduits within the body). The expected path of the medical device within the patient may be programmed prior to the procedure much like a set of roads may be chosen for navigation between two locations using a car's GPS navigation system. The medical device position sensing signal has two independent sources of error: a process error band—position errors induced by sources like patient motion and misregistration—and a measurement error band—position errors inherent to the accuracy of the measurement system. Given a position measurement and knowledge of the anatomical structures, the system algorithm makes a best, safe attempt to represent the location of the medical device within the anatomical conduits. Ultimately, the algorithm decides to display the medical device in one of three positions relative to the anatomical image: within the same anatomical conduit where the device was previously shown, within a new anatomical conduit, or outside of an anatomical conduit. Predetermined distances and tolerances used in the algorithm may be preset in the software, chosen by the physician, or varied based on weighting from the pre-procedure path planning FIG. 10 shows an algorithm that uses the calculated boundaries of anatomical conduits to help determine where to display the medical device relative to the anatomical image. Initial 46 and current 47 positions of the medical device sensor are acquired and the velocity vector for the medical device is calculated 48. The processor searches the anatomical image for the boundaries of the nearest anatomical conduit to the medical device sensor 49. If the sensor position is within a conduit or within a predetermined distance to a conduit 50 and was previously displayed within the same conduit 52, the image of the medical device is shown within that conduit 54. The predetermined distance may be programmed into the algorithm based on the expected error bands for the medical device position sensing system, based on dynamic error updates from the sensor location system, or based on inputs from the operating physician. If the medical device sensor position is within a conduit or within a predetermined distance to a conduit 50 but is not within the same conduit as the previous algorithm cycle, then the velocity vector of the medical device sensor is checked to see whether the path of the sensor matches the path of the new conduit 53 and if the paths match, the medical device is displayed within the image of the new conduit 55. If the medical device sensor is not within a conduit or a predetermined distance to a conduit, then the system searches for a next-nearest conduit within range 51. If a conduit is found in range, conduit path is compared to the sensor path 53 and if the paths match, the medical device is displayed in the new conduit 55. If another conduit is not found within range, the image of the medical device is displayed outside the conduit at the sensed position of the device 56. Similarly, if the sensor is found to be within or near a conduit 50 but was not previously displayed within that conduit 52 and the path of the sensor does not match the path of the conduit 53, the medical device is displayed outside the conduit at its sensed position 56. FIG. 11 shows the application of the algorithm in FIG. 10 to various scenarios. Referring now to FIGS. 10 and 11, the medical device is shown moving within a conduit 57—the conduit shown is similar a femoral artery at the internal iliac branch. The initial medical device position is captured 61. If the sensed position of the device is within the conduit 50 was previously displayed in the conduit 52, the medical device is shown 54 in the image of the conduit 60. If the sensed position of the device is outside the conduit but within a predetermined distance to the conduit 50 and was previously displayed in the conduit 52, then the medical device is shown 59 within the conduit 54. If the medical device sensor is outside the conduit and outside a predetermined distance to a conduit and another conduit is not within range 51, then the medical device is displayed 58 at the actual sensed position 56. The system may also track and record the current and previous sensor position measurements, by doing so for multiple measurements the sensor can be used to map the conduit itself in a breadcrumb type fashion.

Figure 12:
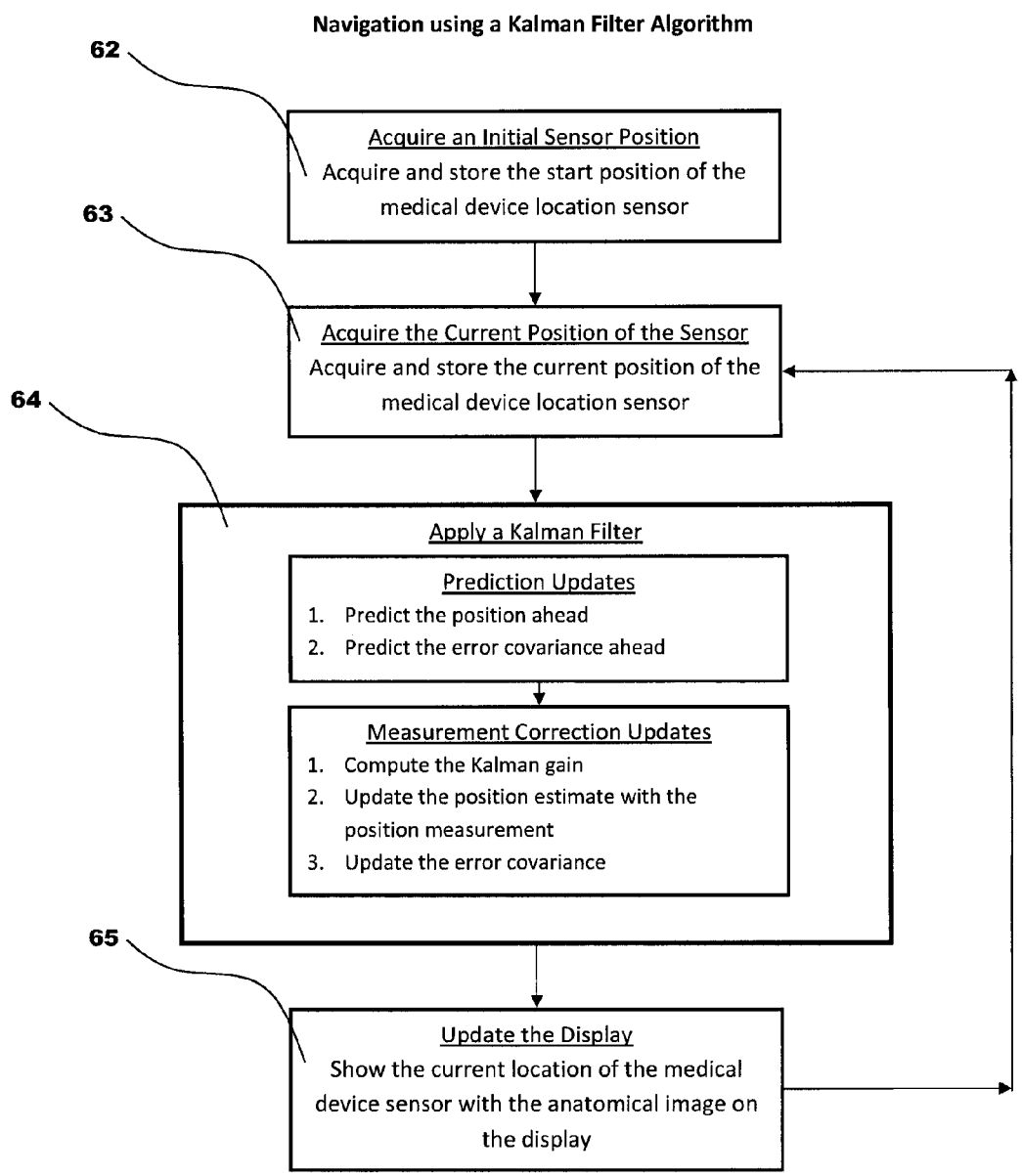
FIG. 12 is a flow chart describing a Kalman Filter algorithm for predicting the position and reducing the error band of a sensored medical device.
Figure 13:
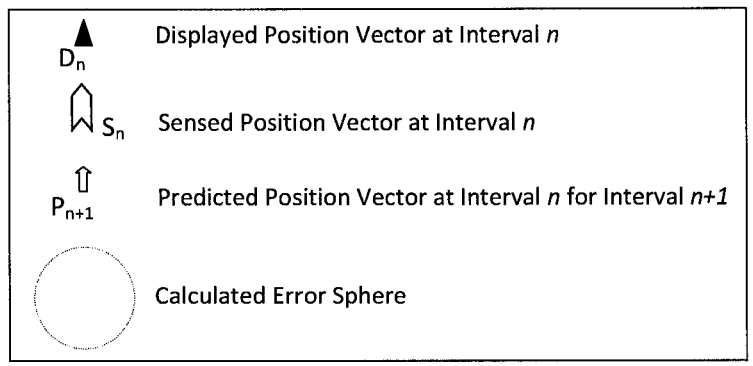
FIG. 13 is a stepwise diagram of the potential results of the flowchart of FIG. 12.
Figure 13:
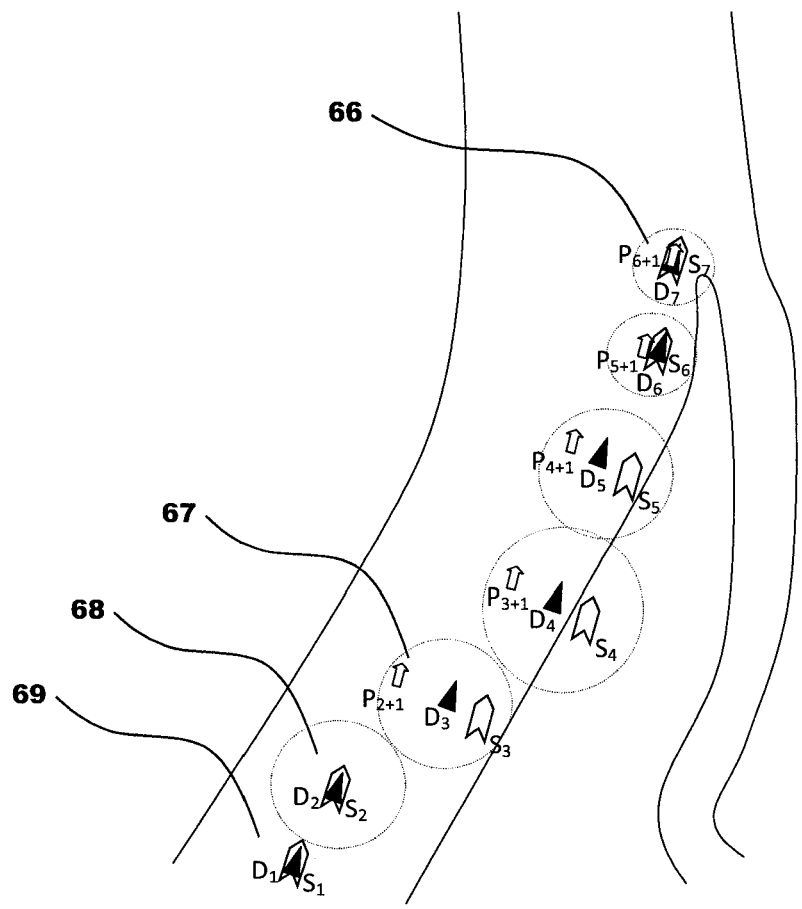

FIGS. 12-13 describe an algorithm that is used within the preferred embodiment to actively characterize and reduce errors in the position sensor data. The algorithm uses known dynamic characteristics of the medical device and position sensor data from the dynamic behavior of the medical device to predict upcoming positions and error bands for the medical device position. A position sensor on the medical device may provide the dynamic behavior of the medical device, by estimating the known characteristics of motion for a hand-operated device, and by incorporating sensors such as accelerometers, encoders, and potentiometers in the handle of the medical device. The algorithm in FIG. 12 first acquires initial 62 and current 63 position data from the medical device position sensor. A Kalman Filter 64 technique, described by R. E. Kalman in 1960, is applied to predict the next sensor position and predict the error band. The Kalman algorithm then uses the data from the cycle to update gain, position estimate and error variables. The location of the medical device is shown with the anatomical image on the display 65 and the algorithmic cycle is repeated. As shown in FIG. 13, as the initial 69 and current 68 sensor positions are collected, a predicted position and error band are calculated 67. As data is collected, the predicted and actual positions converge and the error band decreases 66. The Conduit Boundary algorithm in FIG. 10 and the Kalman Filter algorithm in FIG. 12 may be combined and the error band from the Kalman algorithm may be used to inform the predetermined distances from sensed position to conduit in the Conduit Boundary algorithm.

Additionally, the Kalman algorithm predictions and error bands may be used to determine whether a conduit like a blood vessel is deforming within expected elastic limitations. If the Kalman convergence is robust, but the sensor is predicted to be outside the conduit, the conduit in the three-dimensional segmented anatomical image may be elastically deformed using a commercially available algorithm like Chai 3D with the GEL dynamics engine to model properties such as mass, inertia, elongation, flexion and torsion for the conduit membrane.

Figure 14:
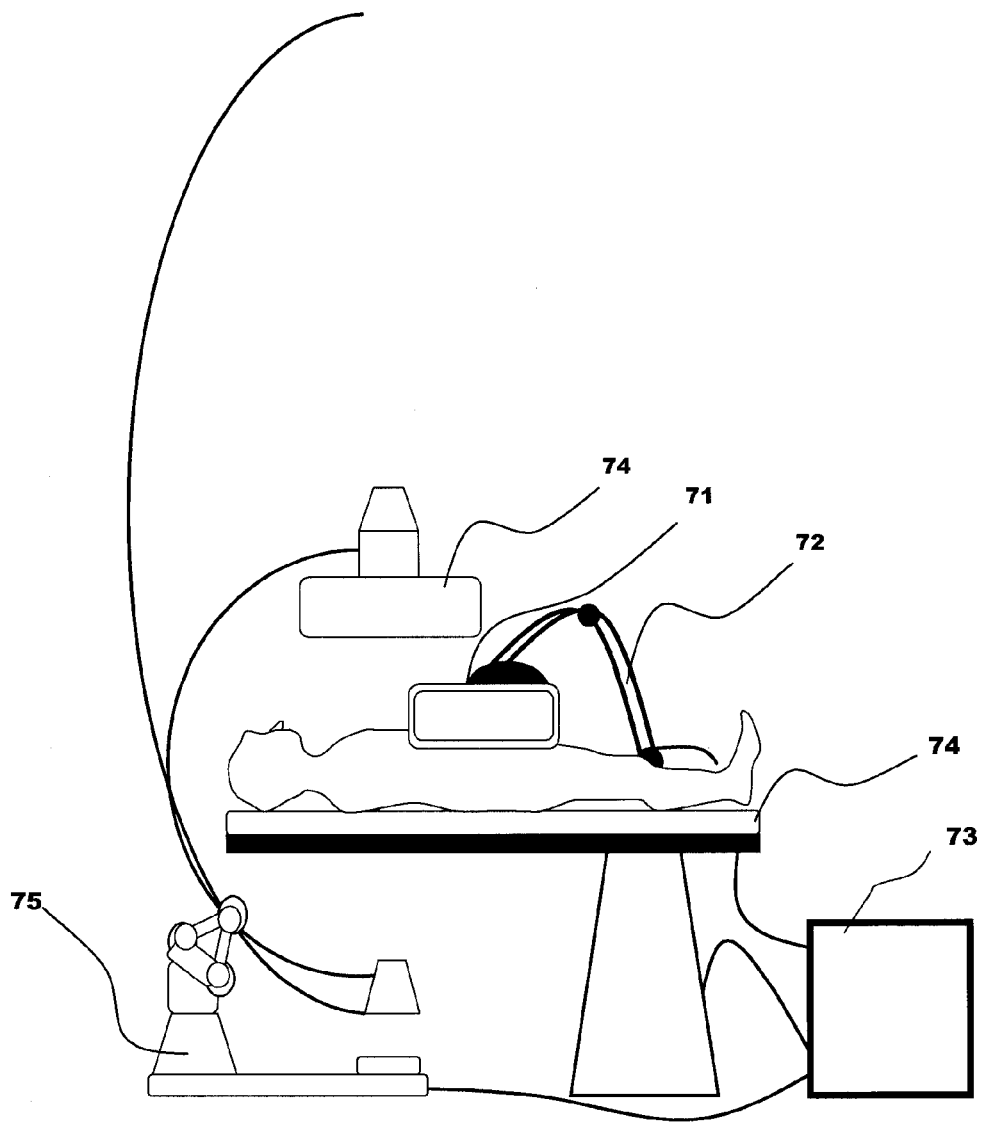
FIG. 14 is a side diagrammatic view of a system for displaying a substantially co-aligned live anatomical image over a patient's anatomy.
Figure 15:
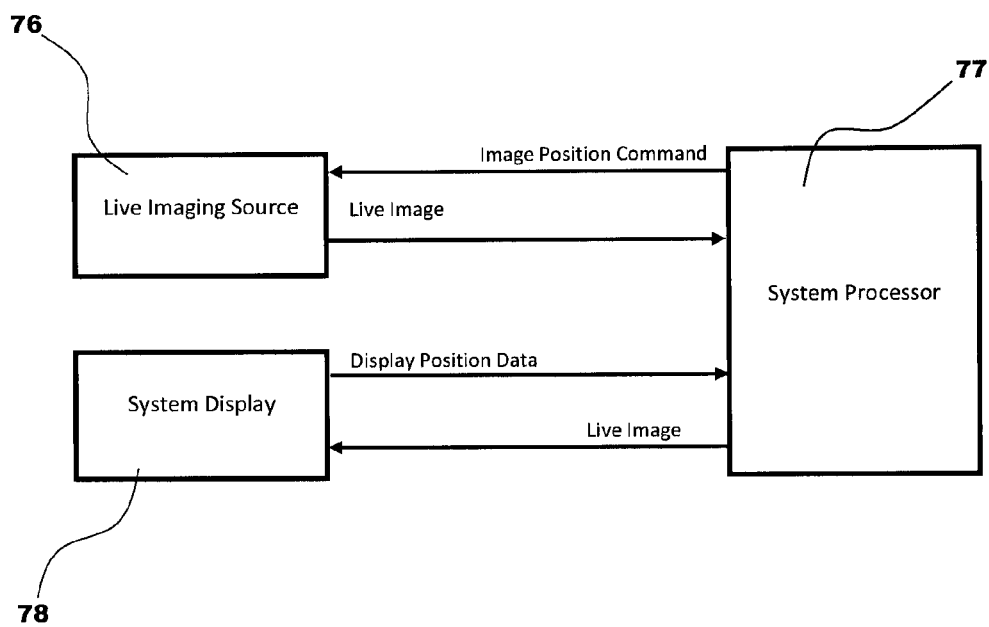
FIG. 15 is a block diagram showing data flow coordinating the image display and live imaging source for the system in FIG. 14.

FIGS. 14-15 describe system embodiments for using at least one live fluoroscopic imaging source during minimally invasive procedures. In FIG. 14, the fluoroscopic imaging detector 70 is located over the patient. The system display 71 is located near the fluoroscopic imaging detector close to the anatomy that is being imaged. The display support 72 holds the display over the patient and allows the user to modify the orientation of the display in at least one degree of motion. The display support is balanced so that the user may easily change the display position with very little force and may be made of materials like carbon fiber composite, which are transparent or translucent to fluoroscopy. The display stays in position if it is not moved by the user. The display position may be tracked with position sensors in each mechanical joint of the display support. Joint position sensors may include optical encoders like those supplied by Canon, US Digital, and Avago; magnetic encoders like those supplied by Timken and Austria Micro Systems, or potentiometers like those supplied by Honeywell and Sensofoil. Alternatively, the display position may be tracked with a free-space sensor located on or coupled to the display. Free-space position sensors include five and six degree-of-freedom electromagnetic sensors like those supplied by Northern Digital Incorporated and Ascension Technology Corporation or optical free-space sensors like those supplied by Northern Digital Incorporated. Data describing the position and orientation of the display is sent to the system processor 73. The system processor is a standard computing system like those supplied by Dell or Hewlett Packard running an operating system like Windows or Linux. The system processor resolves the display position into coordinate system data that is common to the imaging system and sends the data to the imaging system. The display system commands motion of the patient table 74 and/or imaging support system 75 so that the viewing perspective of the live image matches the viewing perspective commanded by the display position. For example, if the user changes the display angle to change the viewing angle of the anatomy, the processor monitors the display angle change and a command is sent from the processor for the imaging system to change the angle of the fluoroscopic imaging detector. An input to translate the display may similarly be monitored and processed and would result in either the patient table or imaging detector panning over the patient to match the motion input at the display by the user. The motions at the display may be scaled within the processor to result in a scaled command to move the imaging source. For example, a 15 degree change in the display angle position may be scaled in the processor at a 1.5:1 factor to result in a 22.5 degree angle change at the imaging system. The scaling factors may be chosen to fit the anatomical workspace so that any resulting mismatch between display angle and imaging angle is well-tolerated by the user. Typically, users tolerate an angular mismatch of up to 30 degrees and translational mismatches of up to 24 inches.

FIG. 15 shows the generic data flow as the live imaging source 76 sends a live image to the processor 77. The processor formats the image and immediately sends it to the system display 78. The display position sensor tracks motion of the display. The display position tracking data is processed by the processor that commands the fluoroscopic equipment to move in such a manner that the image on the display remains substantially aligned with the patient. The processor scales the display position change and converts the position to the same coordinate system as the live imaging source before sending the imaging position that matches the display position to the imaging source.

Figure 16:
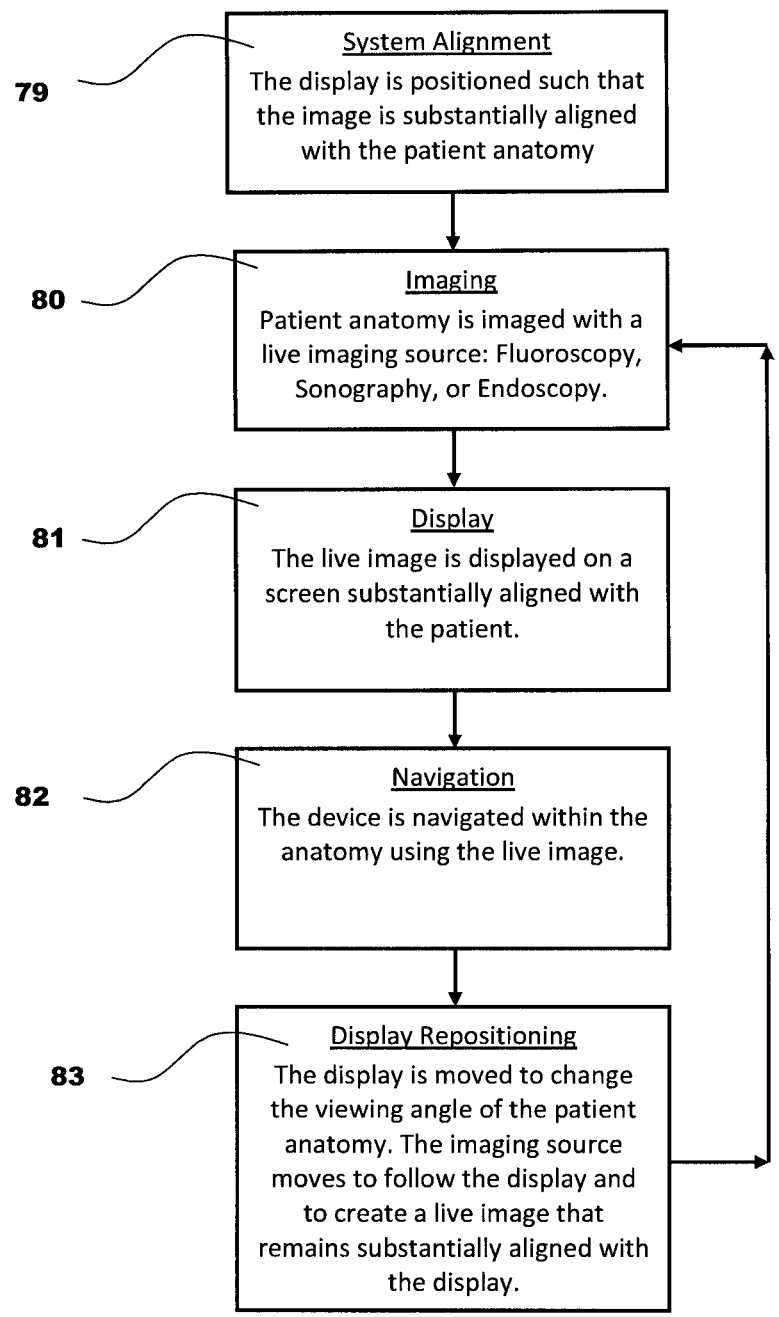
FIG. 16 is a flow chart describing the basic steps for a minimally invasive procedure using a live imaging source and the system for displaying a co-aligned image.

FIG. 16 is a flow chart for a procedure using live imaging. At the start of the procedure, the display and imaging system are aligned during a system alignment step 79. Typically, the display is positioned over the patient anatomy and the display angle is manually set to match the angle of the imaging source. A button is pressed to tell the processor that the display and imaging source are in their aligned start positions. Then the patient anatomy is imaged 80 with the live imaging source. The live imaging source is often fluoroscopy, but may be other common sources of live images like an endoscope or ultrasound probe. The live image is displayed 81 on the system display which is substantially rotationally aligned with the patient's anatomy of interest as the user navigates 82 the medical device within the patient as a live image of the device within the anatomy is shown on the system display. As the user repositions the display 83 to change the view of the device and the anatomy, the system commands the imaging source to similarly reposition in order to achieve the viewing angle and position commanded by the user.

Figure 17:
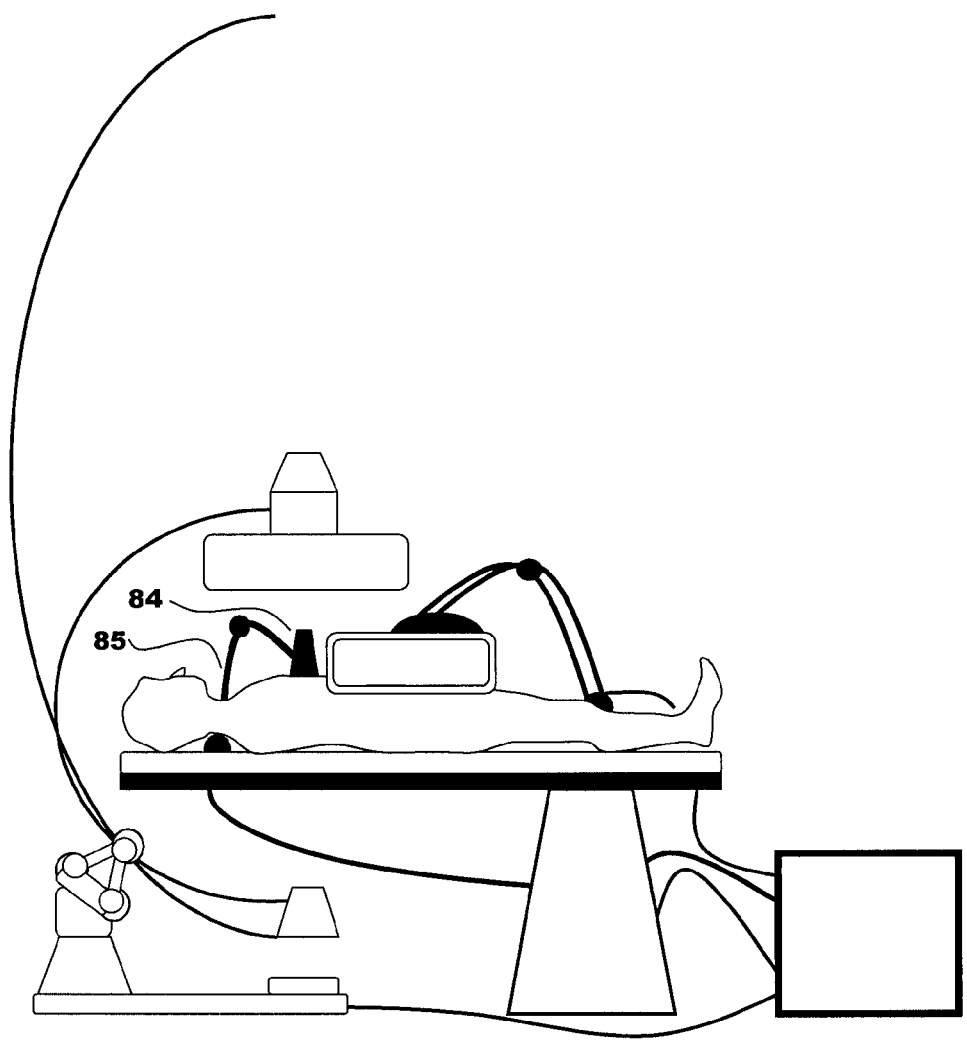
FIG. 17 is a side diagrammatic view of a system for displaying a substantially co-aligned anatomical image with a live fluoroscopic imaging source and a live ultrasound imaging source over a patient's anatomy.

FIG. 17 is a diagram of the same system shown in FIG. 14 with the addition of an ultrasound live image source. The ultrasound support arm 85 is a servo-actuated four-bar linkage system with a mechanical remote center about the contact point between the ultrasound probe 84 and the patient. As the user changes the position of the display, the system calculates an appropriate change in the viewing angle of the ultrasound probe and commands the support arm for the ultrasound probe to reposition so that the ultrasound viewing angle and the display position are substantially co-aligned.

Figure 18:
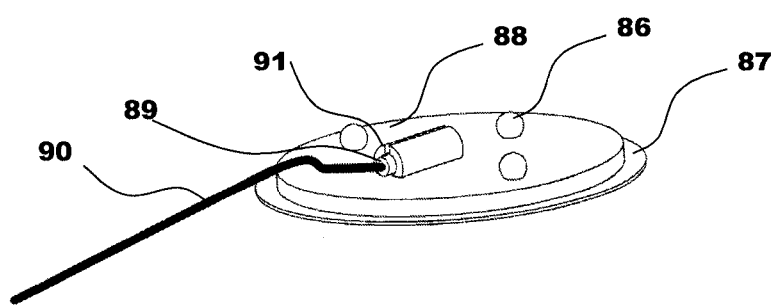
FIG. 18 is a detailed isometric view of an embodiment of the patient reference sensor.

FIG. 18 shows an embodiment of the patient reference sensor. The sensor is affixed to the patient with a skin adhesive layer 87. A rigid plastic disk 88—made of a polymer such as polycarbonate, polypropylene, or nylon—is attached on top of the skin adhesive layer. At least three image-opaque marker spheres 86—in this case MR opaque 4 mm markers containing Gadolinium—are mounted at known unique radial and angular distances from the center of the patch. After imaging is conducted, a electromagnetic coil sensor 89, such as the Ascension model 1080 6-DOF sensor or Northern Digital Incorporated Aurora 6-DOF sensor, may be mounted in a precision snap-fit receptacle in the patch 91. A data transmission cable 90 connects the sensor to the system. Clicking a mouse or other user interface on the visible markers in the segmented or unsegmented anatomical image tells the system the location of the patch, and by extension the sensor, relative to the anatomy.

Figure 19:
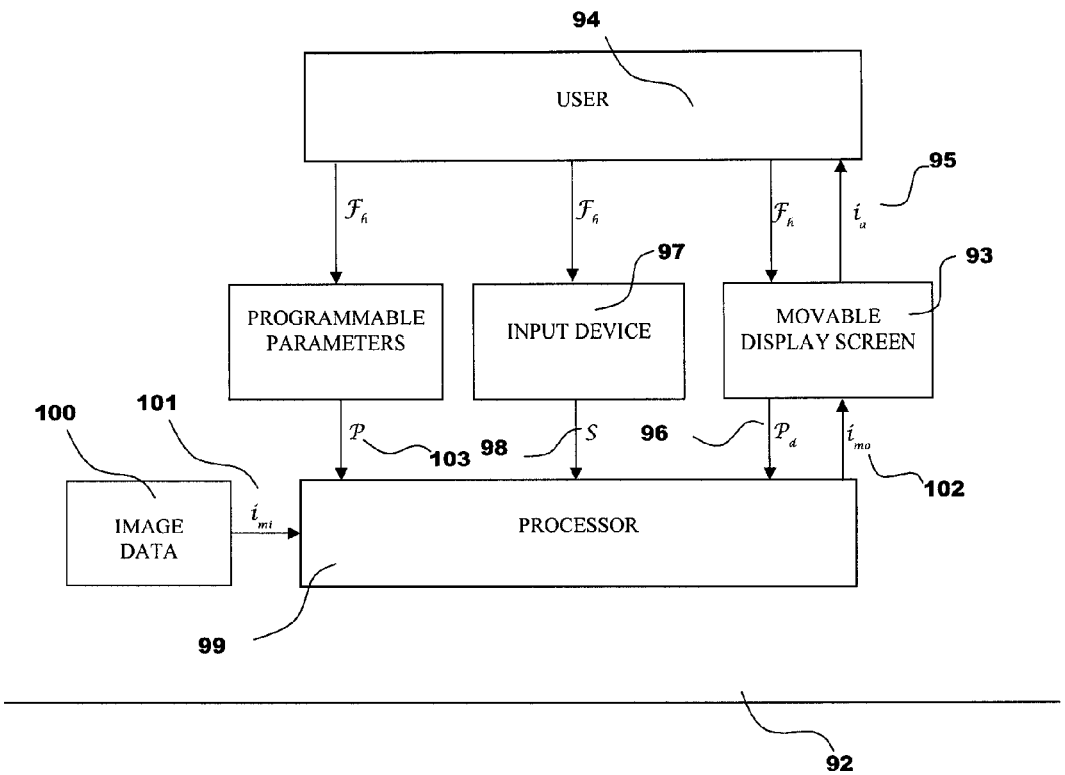
FIG. 19 shows a schematic of system architecture for displaying an image dependant on both the position of the display and the status of the input device.

FIG. 19 shows an embodiment of architecture 92 of a system for displaying an image 95 on a movable display 93 that interacts with a user interface 97. In this embodiment a movable display screen 93 is presented to a user 94. A user 94 can view the image 95 on the display 93 and can move the display in at least one degree of freedom. The image 95 shown on the display 93 is coupled to the position and/or orientation 98 of the display such that moving the display changes the position and/or orientation of the image displayed on the screen. Additionally, the user has an interface via an input device 97, like a foot pedal, palm, finger, or thumb switch, or an active element of the screen itself using touch screen technology, to modify the coupling of the display position and/or orientation to the image. The input device 97 sends signals 93 to the computer 99. Additional signals 96 are sent to the computer to communicate the display's position and/or orientation. The image data 100 is also sent to the computer 99. The image data 100 can be real time x-ray, Ultrasound, video images or previously acquired images or image data sets such as CT, MRI or rotational angiography. Individual programmable parameters 103 are also sent to the computer. These parameters modify the way the image is displayed and may include parameters to set the scaling of the image, the transparency of the image, the texture of the image, the reflectivity of image, the color of the image, the mechanical properties of the image, the resolution of the image, and the digital size of the image. In turn, the computer receives the image file 101, the programmable parameters 103, the display position data 96 and the input status 98 and sends an image data set 102 to the display 93. The screen 93 then receives the image data set 102 and an image 95 is displayed to the user 94.

Figure 20:
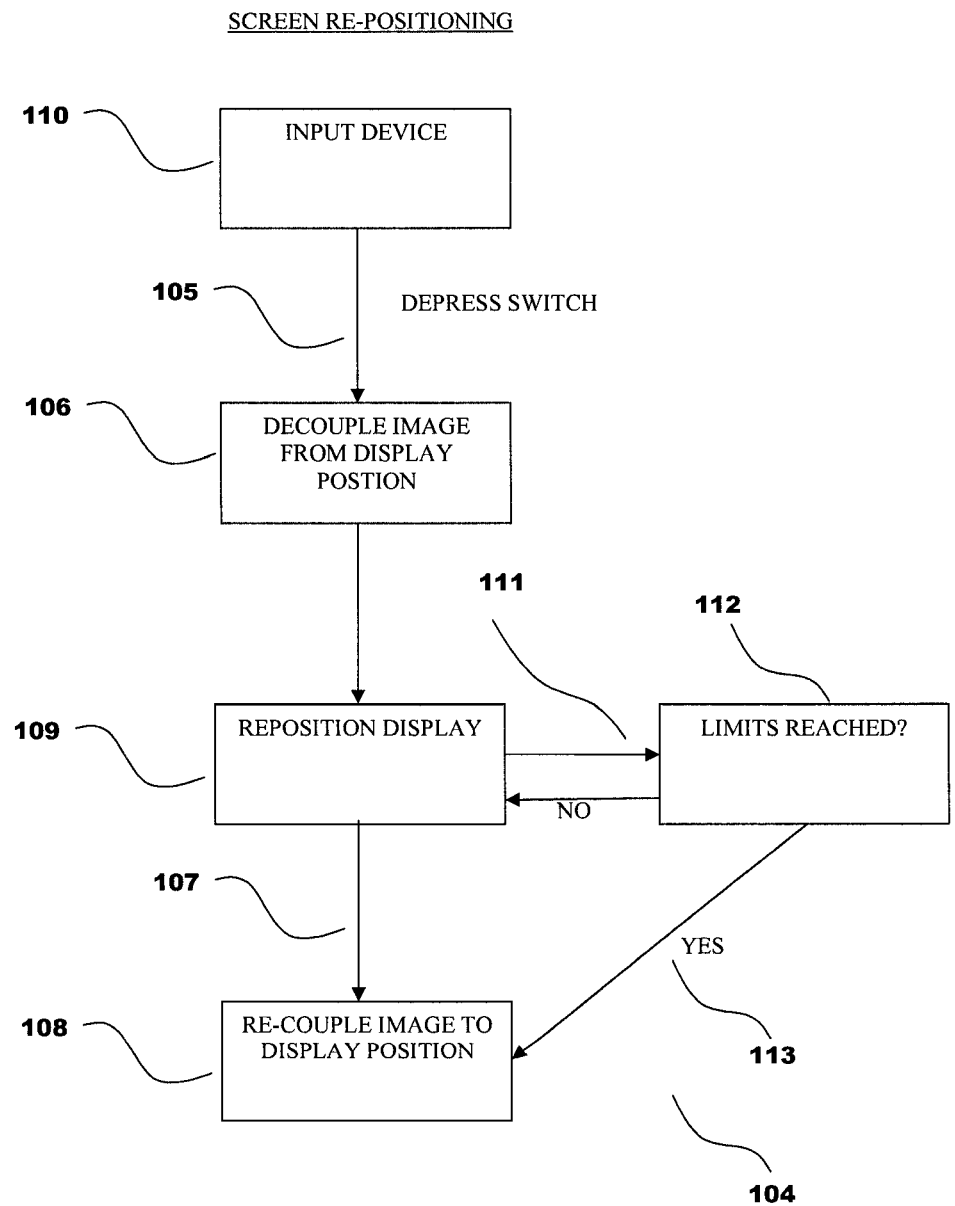
FIG. 20 shows a flow chart for re-positioning the display independently of the image.

FIG. 20 shows an event flow chart 104 for decoupling the relationship of the display position to image for re-positioning the display independently of the image using an input device 110. In the embodiment, the image displayed on the screen is coupled to the screen's position and orientation. Decoupling the image position and/or orientation from the display position and orientation is heretofore referred to as "clutching" which is initiated by a decoupling event and ended by a recoupling event. The term "clutch" as used herein encompasses signal processing, data processing, and/or input techniques which allow, for example, a display to be repositioned while the display position is continually tracked by the processor and at least some of the relationships are temporarily disassociated from the algorithm which is actively updating the image display. For example, a user may 1) activate an input which temporarily disassociates linear translation from the active image position update, 2) move the display, 3) have the image in the display continue to update in rotational orientation but not in translation, and then 4) deactivate the input which temporarily disassociated linear translation from the active image update so that any further manipulations of the display in linear translation result in an image update in the translation axes. As shown, a user can initiate a decoupling event 105 by interacting with the system in some fashion, for instance by depressing a switch. This event 105 is sent to the computer, which, in turn, locks the image in its current state, and the relationship between the display position and/or orientation to the image is broken 106. In this state the display may be repositioned 109 without affecting the displayed image. Once the display is moved to its new position and/or orientation, the switch is released 109. The relationship between the display position and image is then re-established 108. The image is now displayed as a function of the relative motion from this newly repositioned location, as if the display had not been re-positioned. In an alternative explanation of this feature; the user changes the manner in which the image is coupled to the display position and/or the display orientation by introducing location offsets and orientation offsets. Those offsets correspond to the change in position and/or change in orientation of the display when the display is moved in a decoupled state. Preprogrammed values may be included to limit the amount of motion between the first and second positions of the image. During screen repositioning the amount of motion is tracked 111 and compared against limits 112. During screen repositioning, once these limits have been reached 113, the image and display positional relationship will be re-established. To substantially maintain the image to patient relationship and maintain the intuitive feel, the maximum allowable discrepancies are approximately 30 degrees in rotation and 24 inches in position.

Figure 21:
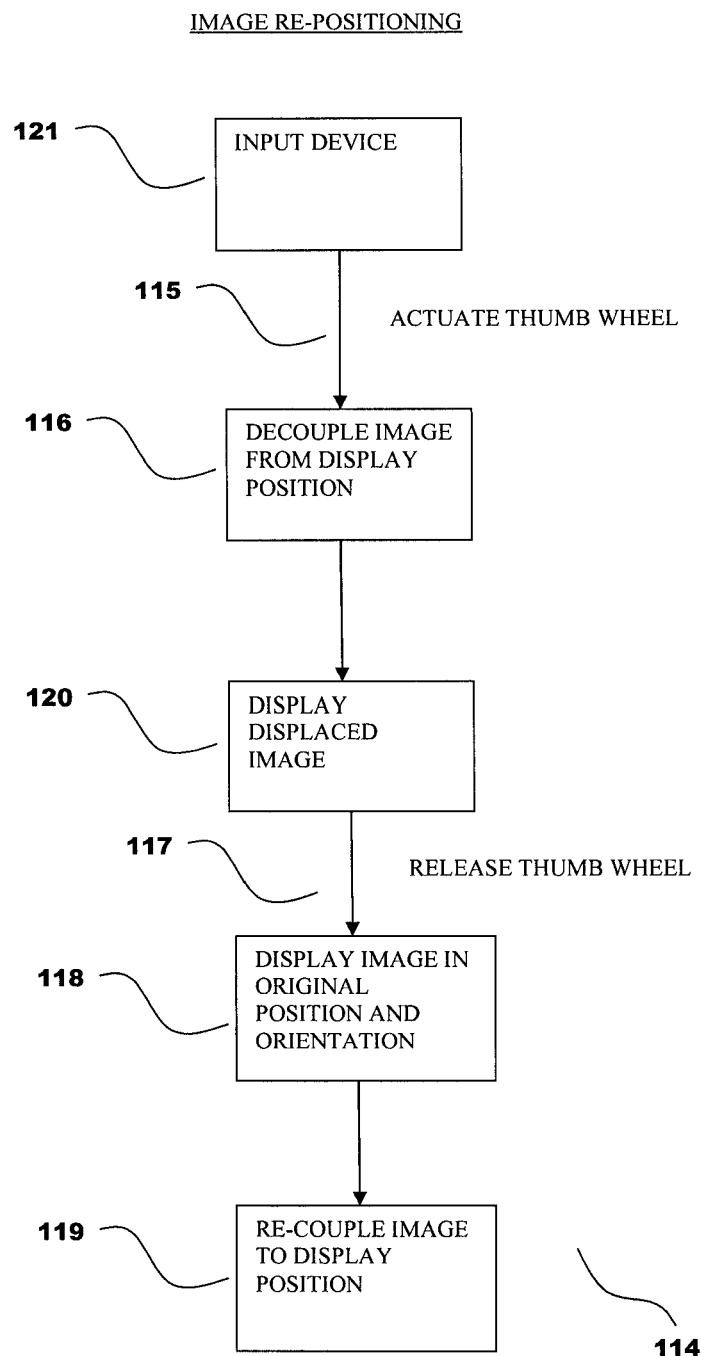
FIG. 21 shows a flow chart for re-positioning the image independently of the display.

FIG. 21 shows an event flow chart 114 for an alternate way to de-couple at least 1 position or orientation axis of the display-image relationship. It may be advantageous from time to time to temporarily decouple the image orientation from the display orientation without moving the display. For instance, the user could actuate 115 using an input device 121 such as a thumb wheel, joystick, or other mechanical device to send a signal to the computer to decouple 116 the image from the display position and rotate, pan, or zoom the image as displayed on the display screen. In the case of touch-screens, the user could use single or multiple fingers to rotate, pan, or zoom the image to a new position. The image would then be correspondingly displaced 120 while the signal or signals are being received by the computer. Once the user releases 117 the thumbwheel, joystick, or touch-screen, the image is returned 118 to its original position and orientation and the image-to-display position relationship is re-established 119 as if the display had not been re-positioned.

Figure 22:
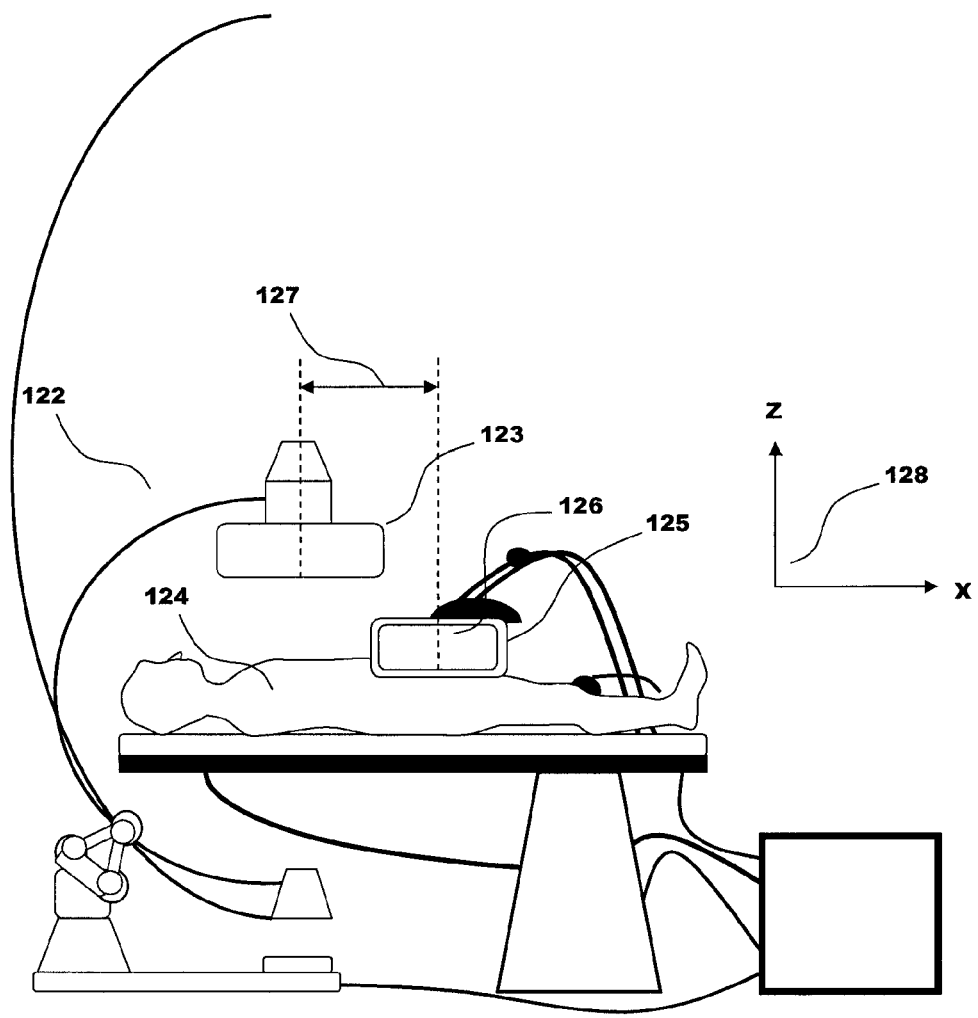
FIG. 22 shows an example of the display translated from the fluoroscopic imaging system.

FIG. 22 shows an example of a translational offset 127 between the imaging system 122 and display 125. In this example, the fluoroscopic imager 136 is placed over the patient's chest 124. The display 125 is placed over the patient's pelvis. This allows the fluoroscopic imaging system 122 to have a clear unimpeded view of the patient's anatomy. Placing the display in the field of view of the imaging system may interfere with the images produced, especially if the display is not fluoroscopically transparent. The image 126 presented to the user is of the patient's chest and is aligned with the patient in all axes and with an offset in the 'x' 128 axis. This offset allows for unimpeded live imaging while maintaining a substantially aligned image. Additionally, the display in this position relative to the fluoroscopy system acts as a radiation shield for the user (not shown) positioned at the display 125.

Figure 23:
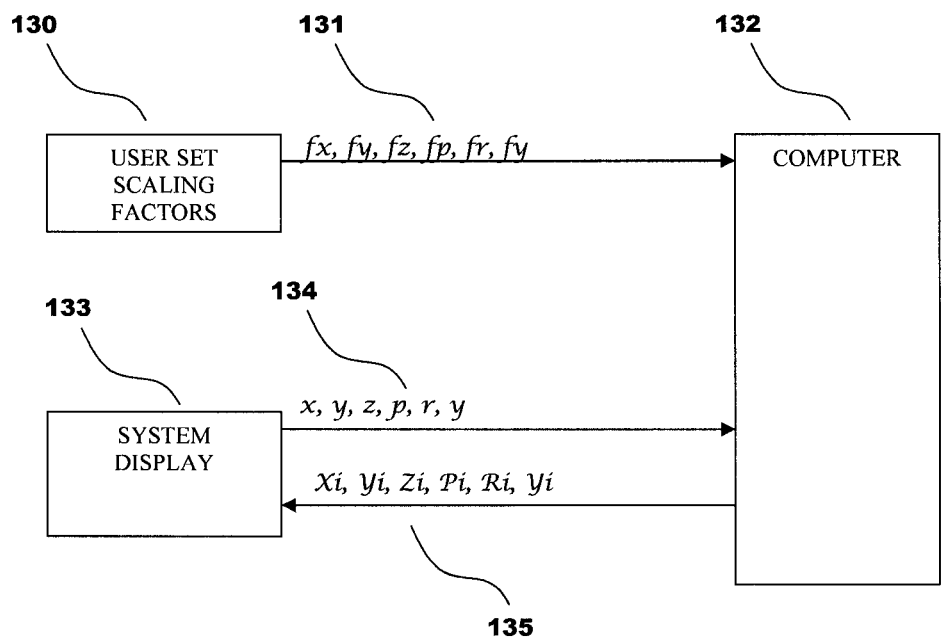
FIG. 23 shows a schematic of system architecture for displaying an image dependant on a scaled position of the display.

FIG. 23 shows a simple architecture 129 for performing image motion scaling. For the purpose of simplicity the above descriptions have largely assumed that the displayed image is a virtual window into the patient. As such there is an inherent 1:1 scaling factor with all aspects of the screen's position and orientation to the image. This 1:1 scaling factor, although reasonable and logical, is, in use, occasionally impractical. The architecture 129 shown allows for user set scaling factors 130, namely fx, fy, fz, fp, fr, fy for scaling motion in the x, y, z, pitch, roll, and yaw axes respectively. The user may enter these scalars 131 into the computer 132. The display 133 position is localized in x, y, z, pitch, roll, and yaw and has the coordinates 134. The computer 132 accordingly multiplies the received system display coordinates 134, by the scalars 131 and displays the image in accordance to the scaled values 135. As an example, if the value of fx is 2 and the screen position is moved 1 mm, then the image will move 2 mm on the screen. As another example if the value of fp is 1.5 and the screen is rotated in the pitch direction by 30 degrees, the image will be rotated in the pitch direction by 45 degrees.

Figure 24:
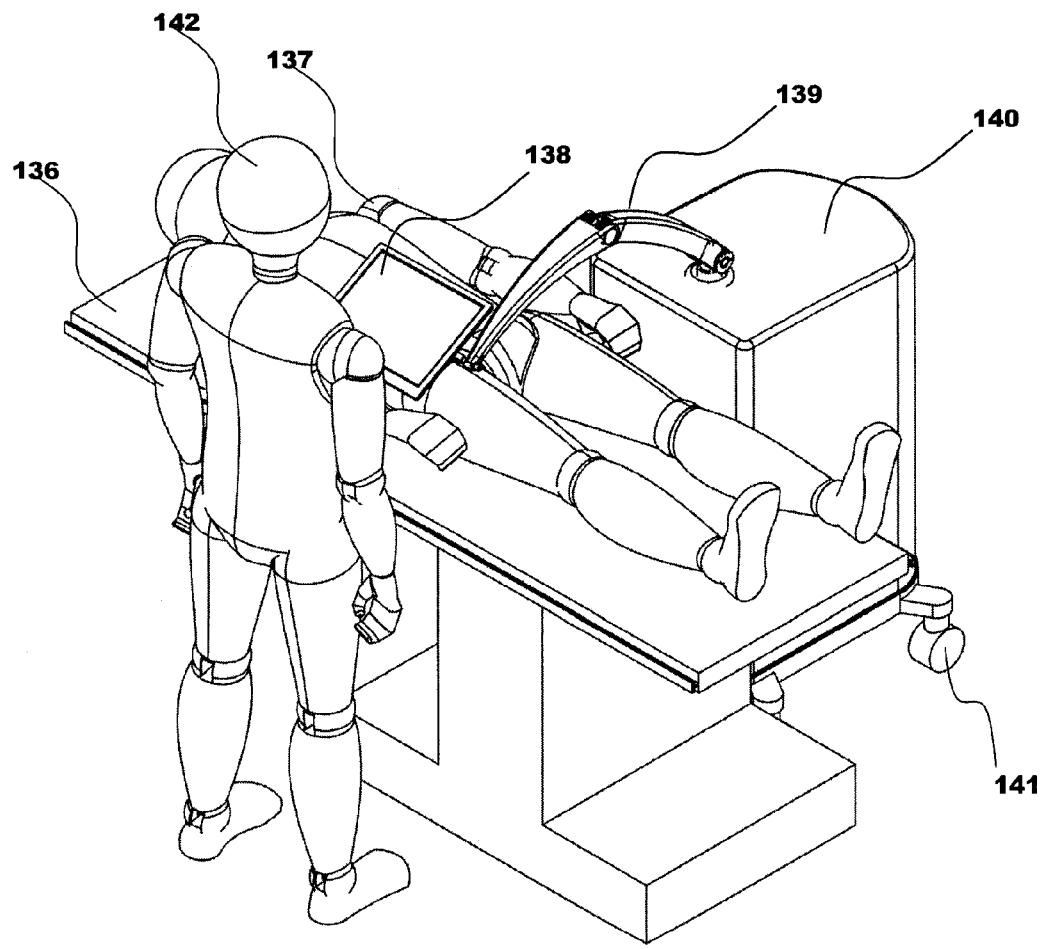
FIG. 24 is an isometric view of an embodiment of the display and support arm positioned on a moveable cart next to the patient table.

FIG. 24 presents an embodiment for positioning a medical image display 138. The display 138 is supported by an arm 139 which is comprised of a movable configuration of linked joints. The arm 139 is mounted to a cart 140 that has lockable wheels 141 so that the arm and display may be placed in different locations for different surgical procedures. The display 138 is presented to the user 142 at a location that is between the user 142 and the patient 137. The patient 137 is lying on a table 136. In this embodiment, the images displayed on the screen 138 may be obtained from a variety of medical imaging sources, including pre-operative and intra-operative images from CT, MRI PET, and rotational angiography, or live images such as ultrasound, fluoroscopy, or endoscopy. In this embodiment, the display 138 is located in the surgical field and may be covered by a sterile drape (not shown for clarity) so that it may be manipulated directly by the operating physician. The display 138 and support arm 139 are movable to reposition the screen during the medical procedure and the position of the display and arm may be tracked during the procedure.

Figure 25:
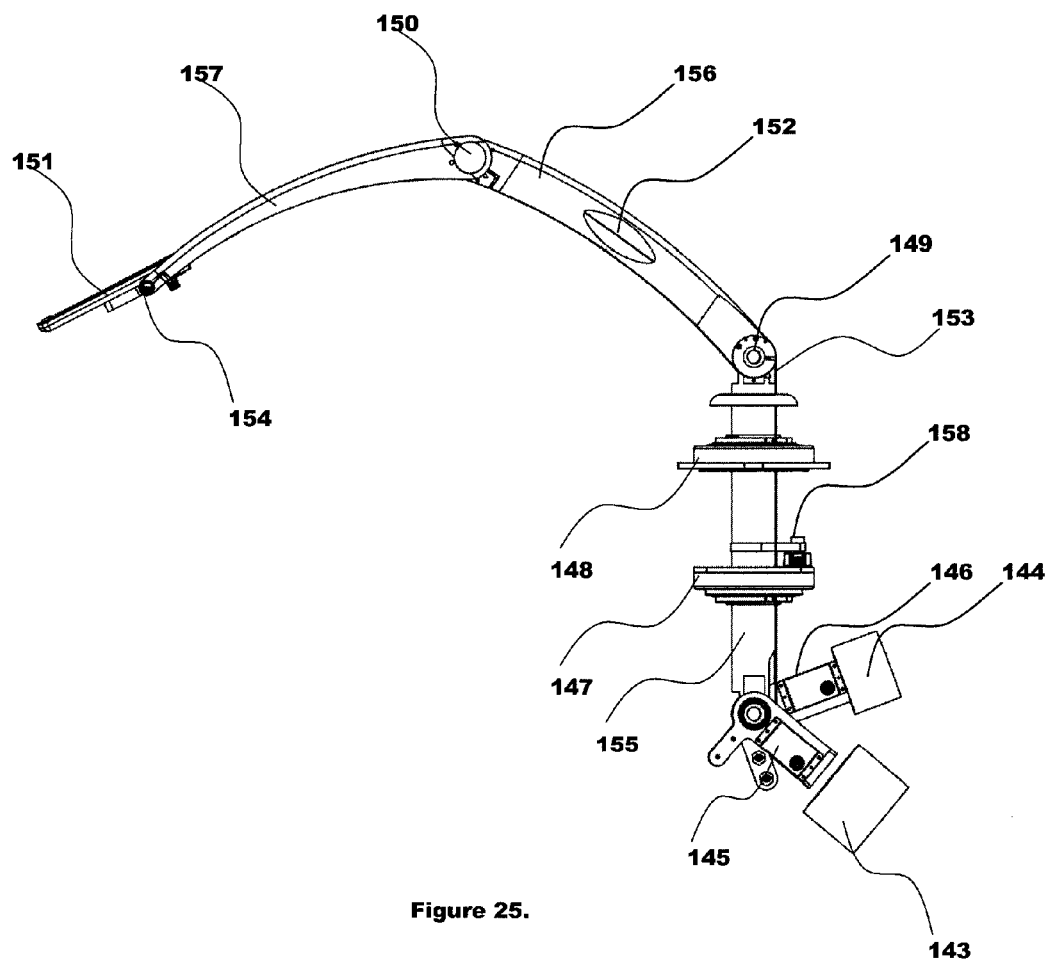
FIG. 25 is side view of the display support arm.

FIG. 25 presents a larger view of the support arm with the cart removed for clarity. In this embodiment, the display 151, is mounted such that the display can be rotated about its center of gravity. Encoder 154 tracks the angular orientation of the display 151. Support links 157 and 156 are pivotally coupled about a horizontal axis at joint 150. Link 156 is pivotally coupled to a horizontal axis at joint 149 on vertical shaft 155. Vertical shaft 155 is supported by bearings 147 and 148 which allow free rotational motion of the shaft. Bearings 147 and 148 are supported by the cart which is depicted in previous FIG. 24. Counterweight 144 provides counterbalancing of arm 157 and display 151 and is coupled via a tension tendon, like rope or wire rope, 152 that runs over joints 149 and 150. Adjustable brakes may be included at joints 149 and 150 to adjust the amount of force required to reposition the display 151. In some embodiments the brakes may be made from Teflon, PPS, or UHMW PE. These materials are the preferred choice of brake materials because their coefficients of static frictions are close to their coefficients of dynamic friction, allowing for smooth repositioning. Counterweight 143 provides counterbalancing for links 156, 157, and display 151 and is coupled via a tension tendon 153 that runs over joint 149. Inclinometers 145 and 146 track the angular position on the links 156 and 157 via the coupled nature provided by the tension tendons. Encoder 158 tracks the rotational position of the base of vertical link 155. The position of the display is determined in a coordinate system affixed to the base of the cart using the signals from the encoders and inclinometers and knowing the fixed length of the links.

Figure 26:
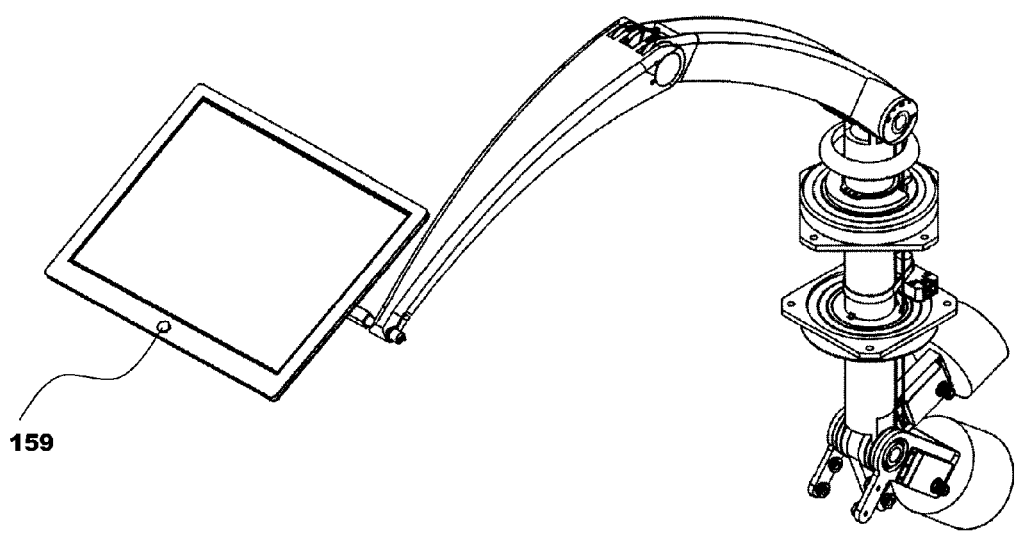
FIG. 26 is an isometric view of the display support arm with a user input.

FIG. 26 shows an isometric view the display support structure with user input button 159.

Figure 27:
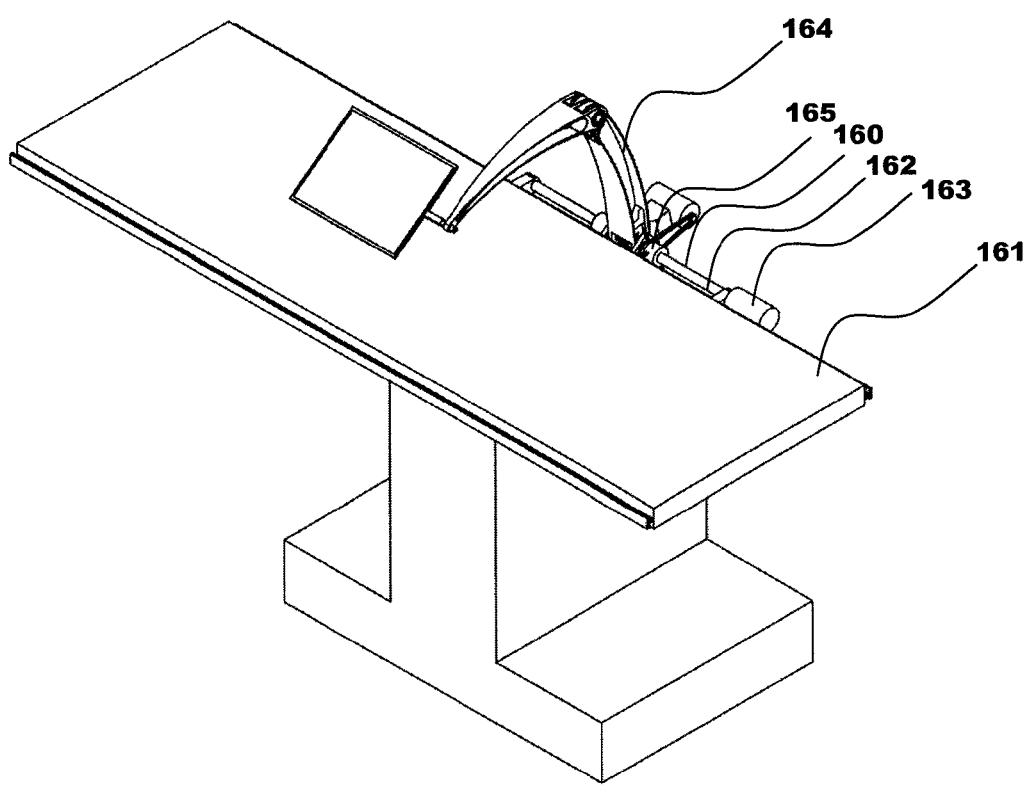
FIG. 27 is an isometric view of a display support arm attached to the patient table.
Figure 28:
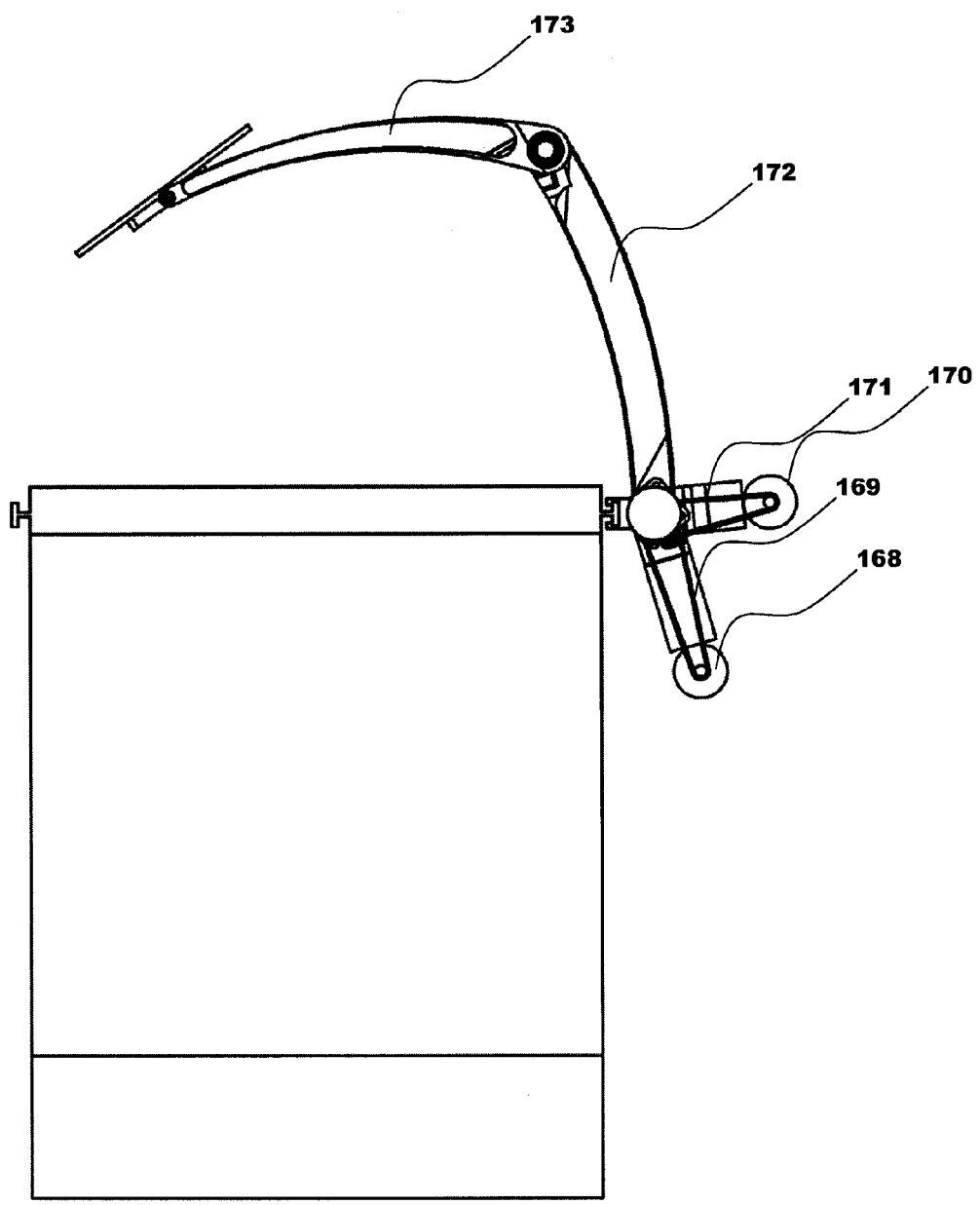
FIG. 28 is a side view of the support arm shown in FIG. 27.

FIGS. 27 and 28 show an alternate configuration of a display support structure. In this embodiment the support structure has a base 160 that is mounted to the table 161. The support structure is mounted to a horizontal leadscrew 162 that is driven by servomotor 163. Link 164 pivots about joint 165 and can travel along a horizontal axis. Servomotor 168 is connected to link 172 via belt 169. Also shown is servomotor 170 connected to belt 171 which is connected to link 173 via a tension tendon as shown in FIG. 25. The servomotors are positioned away from the joint and move with the link to which they are attached and may be positioned to counterbalance the display support structure. In this fashion, the weight of the servomotor reduces the amount of power needed to move the linkage. Motion along the linear axis may be controlled with force sensors that sense the users intended motion and send commands to the servomotor accordingly. Alternatively, motion may be controlled with a joystick or other user input. Additionally, the leadscrew and motor combination may be used to compensate for table motion in the same direction, keeping the display positioned where the physician is standing even thought the table is moved to reposition the patient. Another embodiment replaces the leadscrew and servomotor with a simple linear bearing. Of course, it can be easily imagined by anyone skilled in the art that linear motors, belts or other methods to motorize a linear actuator may replace the leadscrew and servomotor.

Figure 29:
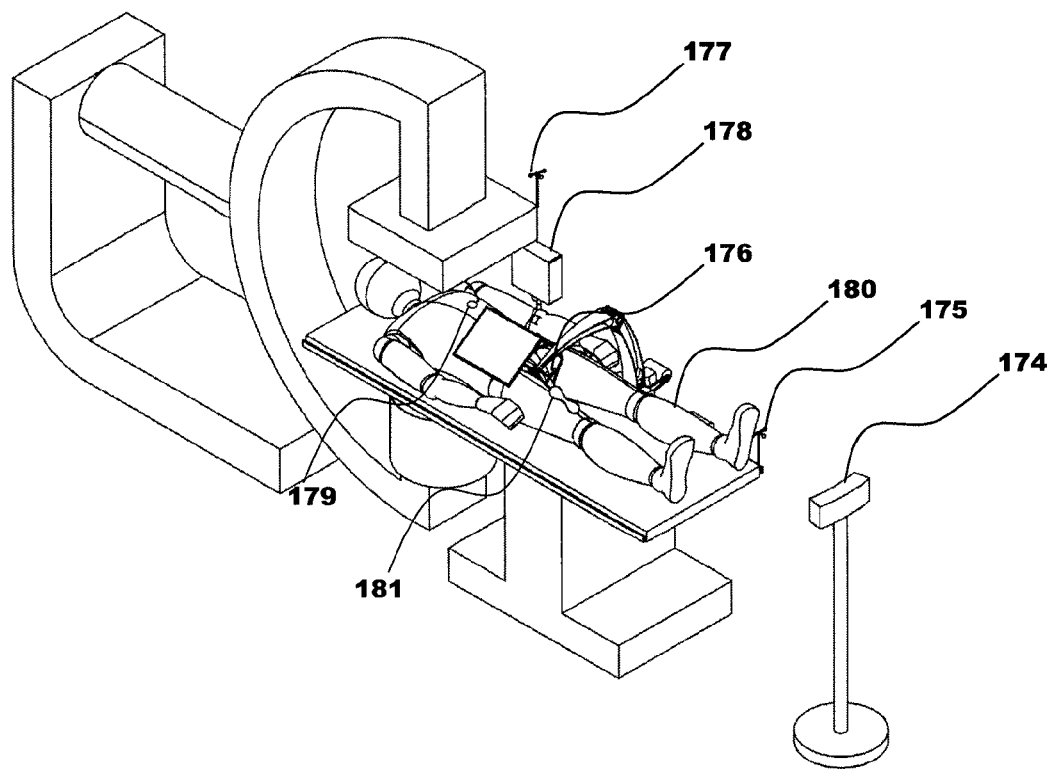
FIG. 29 is an isometric view of a surgical system with multiple tracking systems.

FIG. 29 shows an embodiment where an optical tracking system 174 tracks the position of the table marker 175, the display marker 176, and the fluoroscopy imaging system marker 177. In addition, an electromagnetic tracking system 178 tracks the position of a patient reference marker 179 attached to the patient 180 and a localization sensor attached distal end of a surgical tool 181. It should be noted that any combination of localization systems may be employed to track the various components of the systems. The configuration shown is exemplary and it should be understood that variations of this example exist and may be equally suitable for accomplishing desired results.

Figure 30:
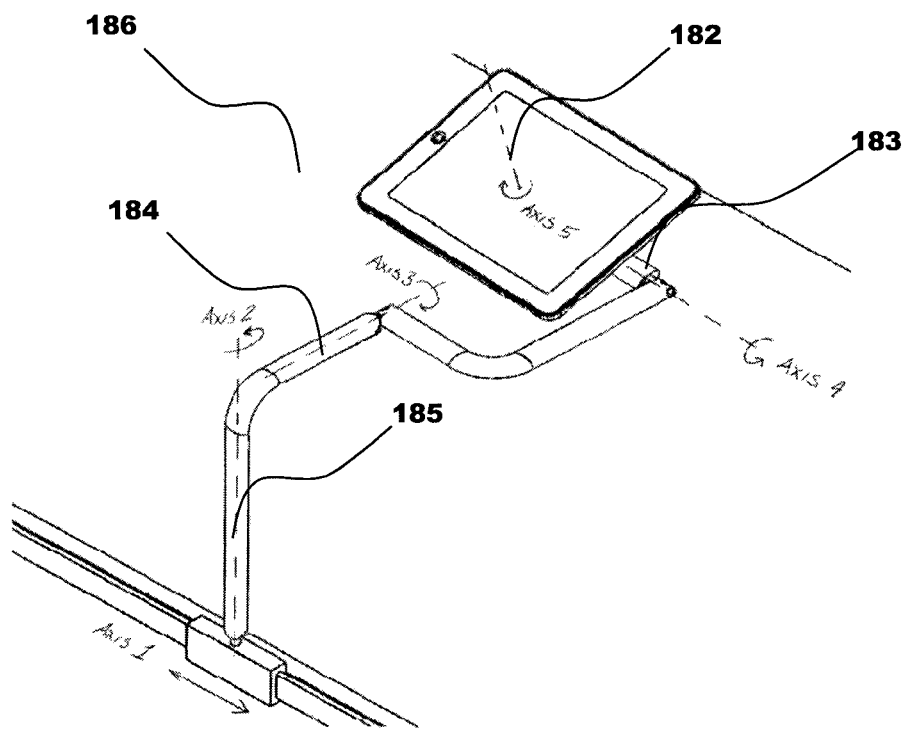
FIG. 30 is an isometric view of a simple display support arm attached to the patient table.

FIG. 30 shows an alternative embodiment for display support arm where the support arm is comprised of a five axis multi-joint device with motion along the table at 186, motion about vertical axis 185, motion about horizontal axis 184, motion about horizontal axis 186 and motion 182 about the display center of gravity. The design provides a high degree of positioning flexibility in all five directions. Additionally, all non-vertical axes pass through the CG of the display. This allows for a lightweight support arm that does not require counterbalancing.

Figure 31:
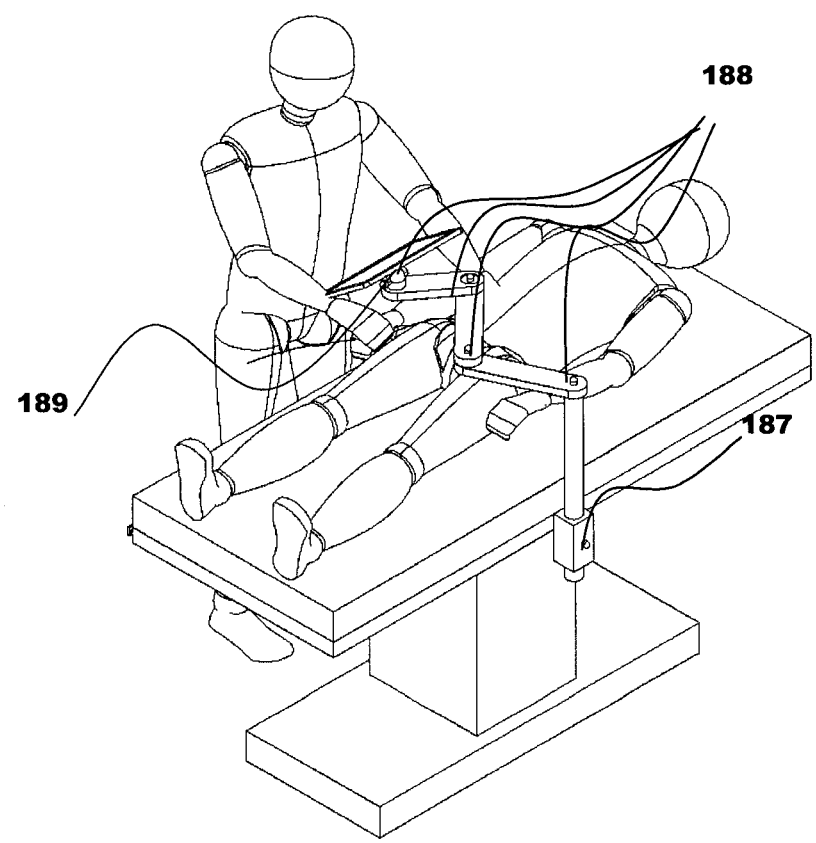
FIG. 31 is an isometric view of an alternate embodiment of a display support arm attached to the patient table.

FIG. 31 shows an embodiment of a three link SCARA type arm with an encoded linear vertical axis 187, four vertical encoded axes 188 and a gimbal joint 189 under the display.

Figure 32:
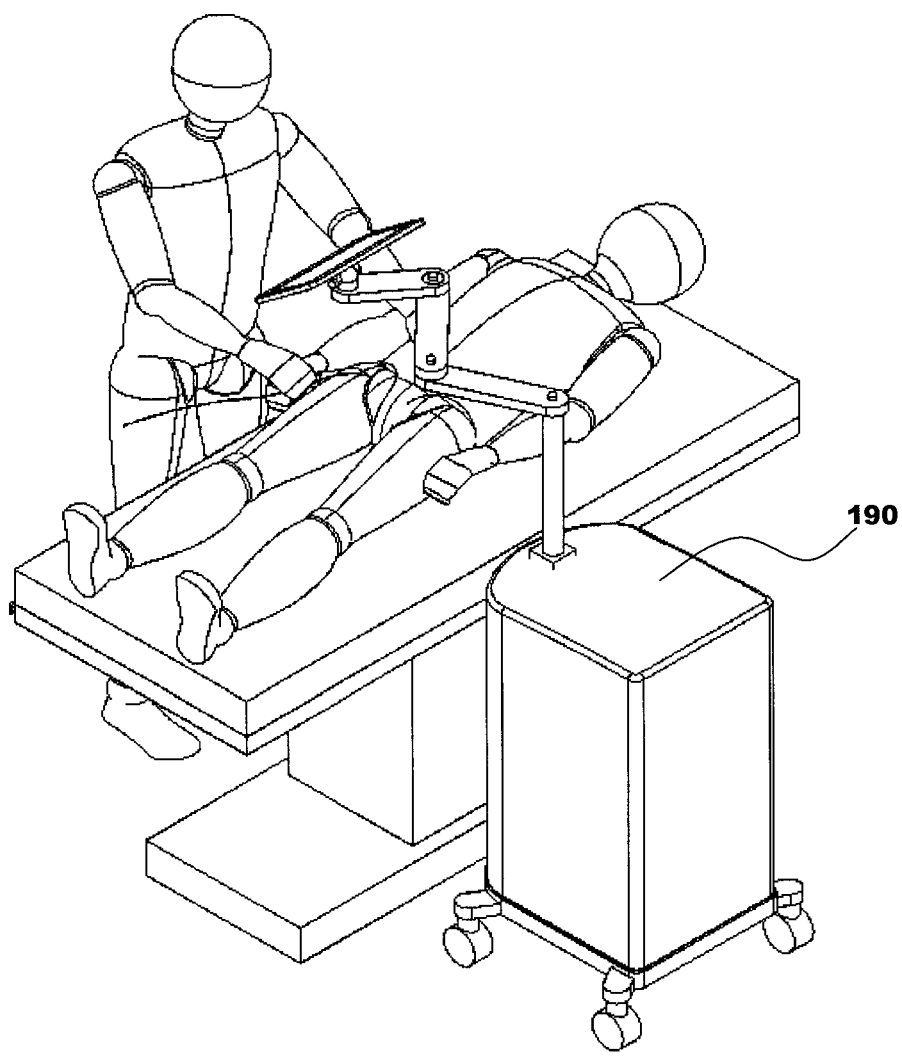
FIG. 32 is an isometric view of an alternate embodiment of a display support arm on a moveable cart.

FIG. 32 shows the support arm of FIG. 31 mounted on a cart 190. The cart allows the display to be positioned in a variety of places within a single room, or in different rooms.

Figure 33:
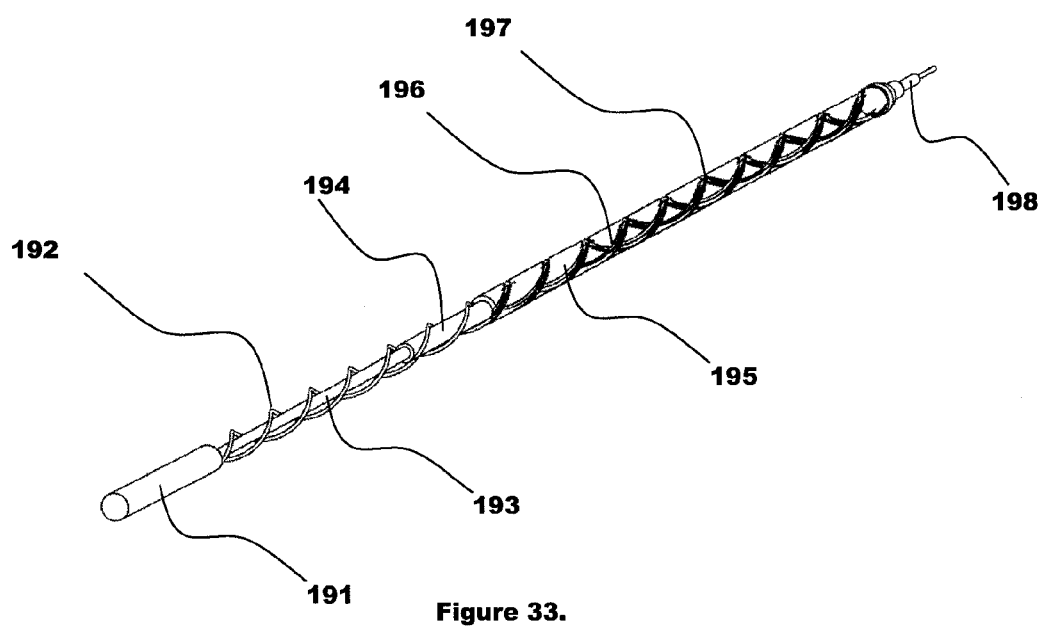
FIG. 33 is an isometric view of the construction of a sensored medical device.

FIG. 33. Shows a simple embodiment of a sensored medical guidewire with the outer jacketing removed for clarity. Guidewires are used in minimally invasive procedures to navigate through the vascular atraumatically. Although many sizes of wires are available, a typical guidewire for simple navigation in the arterial and venous trunk is an 0.035" polymer coated wire like a Terumo Glidewire. A Glidewire has a tapered solid core with a hydrophilic coating. The tapered core allows for good torque transmission, low bending stiffness near the distal end and the coating allows for smooth advancement. Typically, core materials are made from metals, like stainless steel, spring steel, or Nitinol. FIG. 33 shows an EM sensor 191 with its conductive wires 192 traversing down the shaft of the wire, from the distal, to the proximal end. Also shown is a second sensor 194 with its conductive wires 196 helically wrapping around the tapered core 193. The tapered core 193 extends from at least the distal tip of sensor 191 to the proximal end of sensor 194. It should be noted that wire pairs 192 and 196 are preferentially twisted pairs to reduce electrical noise. Also shown is helical cut 197, which allows the wire pairs to wrap down the shaft with minimal increase to the overall construction diameter. The helical cut also preserves the radially symmetric geometry needed for a good performing guide wire with uniform twist. It should be understood that a helical groove could also be cut into the tapered core 193 allowing for wires 192 to run through the center of sensor 194. In all cases at least the portion of the tapered core within the length of the sensors 191 and 194 is comprised of a material of high magnetic permeability such as MuMetal, or permalloy. Finally, the construct may be jacketed with a hydrophilic coating.

Figure 34:
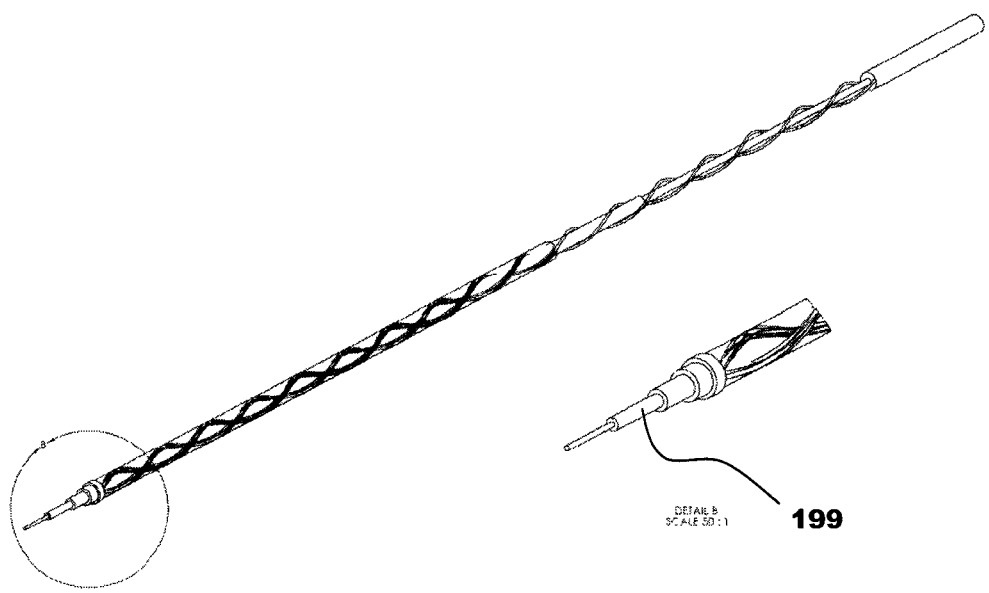
FIG. 34 is a detailed view of a low profile rotatable connector for a sensored medical device.

FIG. 34 shows a detailed section of the connector 199. Wires from the sensors are connected to a connector 199. Connector 199 is constructed with concentric conductive cylinders separated by an insulation layer. The lengths of the cylinders get progressively shorter as they get larger in diameter. The layering of concentric cylinders can be repeated until the needed number of contacts is created. In this example, 4 contacts are needed and shown. This construction allows for a mating connection to rotate along the axis of the wire. This construction also allows for connecting multiple signals within the diameter of the guidewire, in this case 0.035". A series of conductive bands may alternatively be used for connecting multiple signals within the diameter of the guidewire, in this case 0.035".

What is claimed is:

1. A system for displaying an image of a patient anatomy on a moveable display, said system comprising:
    a display screen configured to be moved and aligned with target regions on an exterior of a patient's body;
    a processor configured to receive data representing the patient's anatomy and data representing a position of the display screen in real time, wherein the processor is configured to deliver to the display screen a real-time image representing the patient anatomy in accordance with a first spatial relationship between a position of the patient's actual anatomy and a position of the display screen in real time, the image being updated in real time in response to movement of the display screen in accordance with the first spatial relationship; and
    means on the display screen allowing a user to establish a second spatial relationship between the position of the patient's actual anatomy and the position of the display screen in real time, wherein subsequent movement of the display updates in real-time the image on the display in accordance with said second spatial relationship, wherein the first and second spatial relationships are different from one another, wherein the first and second spatial relationships each comprise a rotational relationship, a translational relationship, or any combination thereof, between the patient's actual anatomy and the display screen, wherein the rotational and translational relationships comprise a plurality of scalars in orthogonal axes, and wherein the plurality of scalars comprises a first scalar in a first axis and a second scalar in a second axis orthogonal to the first axis, the first and second scalars having different magnitudes.

2. A system as in claim 1, wherein the real-time image representing the patient anatomy and delivered to the display screen is scaled, oriented, and positioned on the display screen in accordance with the first spatial relationship,
    wherein the display screen means allows a user to selectively interrupt the first spatial relationship to establish the second spatial relationship such that the image representing the patient's anatomy is scaled, oriented, and positioned on the display screen in accordance the second spatial relationship.

3. A system as in claim 2, wherein the display screen means allow the user to resume the first spatial relationship.

4. A system as in claim 1, wherein the first spatial relationship comprises the translational relationship, and wherein the display screen means allows a user to adjust the translational relationship so that movement of the display screen through a first distance results in movement of the image of the anatomy on the screen over a second distance.

5. A system as in claim 1, wherein the display screen means comprises a user input device on the display screen.

6. A system as in claim 5, wherein the user input device comprises at least one of a tracking pad, roller ball, and a joy stick.

7. A system as in claim 5, wherein the user input device comprises a touch screen.

8. A system as in claim 5, wherein the user input device is voice-activated.

9. A system as in claim 1, further comprising a support for movably holding the display screen relative to the patient's body.

10. A system as in claim 9, wherein the support comprises an articulated arm.

11. A system as in claim 9, wherein the support is sensored to produce the data representing a position of the display screen.

12. A system as in claim 1, further comprising an external tracker for tracking the screen and producing the data representing the position of the display screen.

13. A system as in claim 1, wherein the processor is configured to receive a static image of the patient anatomy from a data file.

14. A system as in claim 1, wherein the processor is configured to receive a real time image of the patient anatomy from a patient imaging device.

15. A system as in claim 1, further comprising an external tracker for tracking movement of the patient's body, wherein the processor is further configured to receive data from the tracker representing the position of the patient's body and to adjust the position of the patient anatomy image on the screen in response to the body movements in real time.

16. A system as in claim 4, wherein the second distance is greater than or less than the first distance traveled by the display screen relative to the patient's actual anatomy.

17. A system as in claim 4, wherein the second distance is the same as the first distance traveled by the display screen relative to the patient's actual anatomy.

18. A system as in claim 12, further comprising an external sensor coupled to the display to determine the position of the display in real-time.

19. A system as in claim 1, further comprising an electromagnetic transmitter configured to (i) generate one or more of the data representing the patient's anatomy or the data representing the position of the display screen in real time and (ii) transmit the one or more of the data representing the patient's anatomy or the data representing the position of the display screen to the processor.

20. A system as in claim 1, further comprising an imaging source configured to capture in the real-time image representing the patient anatomy and transmit said real-time image to the processor.

21. A system as in claim 20, wherein the imaging source comprises a fluoroscopic imaging system.

22. A system as in claim 20, wherein the processor is configured to command the imaging source to reposition in response to repositioning of the display screen.

23. A system as in claim 1 wherein the one or more of the first or second spatial relationships comprise both rotational and translational relationships.

24. A system as in claim 1, wherein both the first and second spatial relationships comprise rotational relationships.

25. A system as in claim 4, wherein the first and second distances are different, and wherein the translational relationship of the first spatial relationship comprises a scaling factor selected by the user.

26. A system as in claim 1, wherein the plurality of scalars comprises a third scalar in a third axis orthogonal to both the first and second axes.

27. A system as in claim 1, wherein magnitudes for the plurality of scalars are user selectable.

* * * * *